United States Patent
Sato et al.

(10) Patent No.: US 11,414,655 B2
(45) Date of Patent: Aug. 16, 2022

(54) EFFICIENT METHOD FOR PRODUCING AMBREIN

(71) Applicants: Niigata University, Niigata (JP); Adeka Corporation, Tokyo (JP)

(72) Inventors: Tsutomu Sato, Niigata (JP); Tsutomu Hoshino, Niigata (JP); Toshihiko Takehana, Tokyo (JP); Seiji Koike, Tokyo (JP); Koichi Shigeno, Tokyo (JP)

(73) Assignees: Niigata University, Niigata (JP); Adeka Corporation, Tokyo (JP)

( * ) Notice: Subject to any disclaimer, the term of this patent is extended or adjusted under 35 U.S.C. 154(b) by 0 days.

(21) Appl. No.: 16/642,149

(22) PCT Filed: Aug. 31, 2018

(86) PCT No.: PCT/JP2018/032418
§ 371 (c)(1),
(2) Date: Feb. 26, 2020

(87) PCT Pub. No.: WO2019/045058
PCT Pub. Date: Mar. 7, 2019

(65) Prior Publication Data
US 2020/0354754 A1 Nov. 12, 2020

(30) Foreign Application Priority Data
Sep. 1, 2017 (JP) .............................. JP2017-168128

(51) Int. Cl.
*C12N 9/90* (2006.01)
*C12P 7/02* (2006.01)
*C12N 1/20* (2006.01)

(52) U.S. Cl.
CPC ................. *C12N 9/90* (2013.01); *C12N 1/20* (2013.01); *C12P 7/02* (2013.01)

(58) Field of Classification Search
CPC ....................................................... C12N 9/90
See application file for complete search history.

(56) References Cited

U.S. PATENT DOCUMENTS 9,447,404 B2 * 9/2016 Breuer ...................... C12N 9/90
10,844,407 B2 * 11/2020 Sato ......................... C12N 9/90

FOREIGN PATENT DOCUMENTS

| JP | H10-236996 A | 9/1998 |
| WO | 2015/033746 A1 | 3/2015 |

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Morgan, Lewis & Bockius LLP

(57) ABSTRACT

An object of the present invention is to provide a method for preparing ambrein, which can easily and efficiently obtain the ambrein.
The object can be solved by a mutated tetraprenyl-β-curcumene cyclase wherein
(1) a 4th amino acid residue of a DXDD motif, aspartic acid, is substituted with an amino acid other than aspartic acid, and
(2) an amino acid adjacent to the N-terminus of a (A/S/G) RX(H/N)XXP motif is substituted with an amino acid other than tyrosine, or a 4th amino acid of the GXGX(G/A/P) motif is substituted with an amino acid other than leucine.

11 Claims, 8 Drawing Sheets

Specification includes a Sequence Listing.

(56) References Cited

OTHER PUBLICATIONS

0A1Q8UV62_BACME. UnitPortKB/TrEMBL. Apr. 12, 2017.*
Ueda et al., "Creation of squalene-ambrein cyclase: ambrein can synthesized from squalene by one enzyme through two pathways," Lecture abstracts of the conference of the Society for Biotechnology, Japan, 69: 321 (2017).
Murakami et al., "Analysis of catalytic mechanism of bifunctional triterpene/sesquarterpene cyclase," Lecture abstracts of the 2017 conference of JSBBA, lecture No. 3C11p11 (2017).
Sato et al., "Functional Analysis of the DXDDTA Motif in Squalene-Hopene Cyclase by Site-directed Mutagenesis Experiments: Initiation Site of the Polycyclization Reaction and Stabilization Site of the Carbocation Intermediate of the Initially Cyclized A-Ring," Bioscience, Biotechnology, and Biochemistry, 63 (12): 2189-2198 (1999).
Sato et al., "Catalytic Function of the Residues of Phenylalanine and Tyrosine Conserved in Squalene-Hopene Cyclases," Bioscience, Biotechnology, and Biochemistry, 65 (10): 2233-2242 (2001).
Ueda et al., "Cyclization of Squalene from Both Termini: Identification of an Onoceroid Synthase and Enzymatic Synthesis of Ambrein," Journal of the American Chemical Society, 135: 18335-18338 (2013).
Fujiwara et al., "New total synthesis of (+)-ambrein," Tetrahedron: Asymmetry, 17: 3037-3045 (2006).
Sato et al., "Functional Analyses of Tyr420 and Leu607 of Alicyclobacillus acidocaldarius Squalene-Hopene Cyclase. Neoachillapentaene, a Novel Triterpene with the 1,5,6-Trimethylcyclohexene Moiety . . . " Bioscience, Biotechnology, and Biochemistry, 66 (8): 1660-1670 (2002).
Sato et al., "Bifunctional Triterpene/Sesquarterpene Cyclase: Tetraprenyl-beta-curcumene Cyclase Is Also Squalene Cyclase in Bacillus megaterium," Journal of the American Chemical Society, 133: 17540-17543 (2011).
International Search Report issued in corresponding International Patent Application No. PCT/JP2018/032418 dated Dec. 4, 2018.
Extended European Search Report issued in corresponding European Patent Application No. 18850283.5 dated Jul. 1, 2021.
Dang et al., "Site directed mutagenesis of squalene-hopene cyclase: altered substrate specificity and product distribution," Chemistry & Biology, 7 (8): 643-649 (2000).
Poralla, "The Possible Role of a Repetitive Amino Acid Motif in Evolution of Triterpenoid Cyclases," Bioorganic & Medicinal Chemistry Letters, 4 (2): 285-290 (1994).
Yamabe et al., "Construction of an artificial system for ambrein biosynthesis and investigation of some biological activities of ambrein," Scientific Reports, 10: 19643 (2020).
Wendt et al., "Structure and Function of a Squalene Cyclase," Science, 277: 1811-1815 (1997).
Prisic et al., "Probing the Role of the DXDD Motif in Class II Diterpene Cyclases," ChemBioChem, 8: 869-874 (2007).

* cited by examiner (A)

```
WildType     1 MIILLKEVQL EIQRRIAYLR PTQKNDGSFR YCFETGVMPD AFLIMLLRTF DLDKEVLIKQ  60
Y167A/D373C  1 MIILLKEVQL EIQRRIAYLR PTQKNDGSFR YCFETGVMPD AFLIMLLRTF DLDKEVLIKQ  60
D373C/L596A  1 MIILLKEVQL EIQRRIAYLR PTQKNDGSFR YCFETGVMPD AFLIMLLRTF DLDKEVLIKQ  60

WildType    61 LTERIVSLQN EDGLWTLFDD EEHNLSATIQ AYTALLYSGY YQKNDRILRK AERYIIDSGG 120
Y167A/D373C 61 LTERIVSLQN EDGLWTLFDD EEHNLSATIQ AYTALLYSGY YQKNDRILRK AERYIIDSGG 120
D373C/L596A 61 LTERIVSLQN EDGLWTLFDD EEHNLSATIQ AYTALLYSGY YQKNDRILRK AERYIIDSGG 120

WildType   121 ISRAHFLTRW MLSVNGLYEW PKLFYLPLSL LLVPTYVPLN FYELSTYARI HFVPMMVAGN 180
Y167A/D373C 121 ISRAHFLTRW MLSVNGLYEW PKLFYLPLSL LLVPTYVPLN FYELSTAARI HFVPMMVAGN 180
D373C/L596A 121 ISRAHFLTRW MLSVNGLYEW PKLFYLPLSL LLVPTYVPLN FYELSTYARI HFVPMMVAGN 180

WildType   181 KKFSLTSRHT PSLSHLDVRE QKQESEETTQ ESRASIFLVD HLKQLASLPS YIHKLGYQAA 240
Y167A/D373C 181 KKFSLTSRHT PSLSHLDVRE QKQESEETTQ ESRASIFLVD HLKQLASLPS YIHKLGYQAA 240
D373C/L596A 181 KKFSLTSRHT PSLSHLDVRE QKQESEETTQ ESRASIFLVD HLKQLASLPS YIHKLGYQAA 240

WildType   241 ERYMLERIEK DGTLYSYATS TFFMIYGLLA LGYKKDSFVI QKAIDGICSL LSTCSGHVHV 300
Y167A/D373C 241 ERYMLERIEK DGTLYSYATS TFFMIYGLLA LGYKKDSFVI QKAIDGICSL LSTCSGHVHV 300
D373C/L596A 241 ERYMLERIEK DGTLYSYATS TFFMIYGLLA LGYKKDSFVI QKAIDGICSL LSTCSGHVHV 300

WildType   301 ENSTSTVWDT ALLSYALQEA GVPQQDPMIK GTTRYLKKRQ HTKLGDWQFH NPNTAPGGWG 360
Y167A/D373C 301 ENSTSTVWDT ALLSYALQEA GVPQQDPMIK GTTRYLKKRQ HTKLGDWQFH NPNTAPGGWG 360
D373C/L596A 301 ENSTSTVWDT ALLSYALQEA GVPQQDPMIK GTTRYLKKRQ HTKLGDWQFH NPNTAPGGWG 360

WildType   361 FSDINTNNPD LDDTSAAIRA LSRRAQTDTD YLESWQRGIN WLLSMQNKDG GFAAFEKNTD 420
Y167A/D373C 361 FSDINTNNPD LDCTSAAIRA LSRRAQTDTD YLESWQRGIN WLLSMQNKDG GFAAFEKNTD 420
D373C/L596A 361 FSDINTNNPD LDCTSAAIRA LSRRAQTDTD YLESWQRGIN WLLSMQNKDG GFAAFEKNTD 420

WildType   421 SILFTYLPLE NAKDAATDPA TADLTGRVLE CLGNFAGMNK SHPSIKAAVK WLFDHQLDNG 480
Y167A/D373C 421 SILFTYLPLE NAKDAATDPA TADLTGRVLE CLGNFAGMNK SHPSIKAAVK WLFDHQLDNG 480
D373C/L596A 421 SILFTYLPLE NAKDAATDPA TADLTGRVLE CLGNFAGMNK SHPSIKAAVK WLFDHQLDNG 480

WildType   481 SWYGRWGVCY IYGTWAAITG LRAVGVSASD PRIIKAINWL KSIQQEDGGF GESCYSASLK 540
Y167A/D373C 481 SWYGRWGVCY IYGTWAAITG LRAVGVSASD PRIIKAINWL KSIQQEDGGF GESCYSASLK 540
D373C/L596A 481 SWYGRWGVCY IYGTWAAITG LRAVGVSASD PRIIKAINWL KSIQQEDGGF GESCYSASLK 540

WildType   541 KYVPLSFSTP SQTAWALDAL MTICPLKDQS VEKGIKFLLN PNLTEQQTHY PTGIGLPGQF 600
Y167A/D373C 541 KYVPLSFSTP SQTAWALDAL MTICPLKDQS VEKGIKFLLN PNLTEQQTHY PTGIGLPGQF 600
D373C/L596A 541 KYVPLSFSTP SQTAWALDAL MTICPLKDQS VEKGIKFLLN PNLTEQQTHY PTGIGAPGQF 600

WildType   601 YIQYHSYNDI FPLLALAHYA KKHSS                                       625
Y167A/D373C 601 YIQYHSYNDI FPLLALAHYA KKHSS                                       625
D373C/L596A 601 YIQYHSYNDI FPLLALAHYA KKHSS                                       625
```

Figure 9

```
WildType   1 MIILLKEVQL EIQRRIAYLR PTQKNDGSFR YCFETGVMPD AFLIMLLRTF DLDKEVLIKQ  60
L596A      1 MIILLKEVQL EIQRRIAYLR PTQKNDGSFR YCFETGVMPD AFLIMLLRTF DLDKEVLIKQ  60
L596F      1 MIILLKEVQL EIQRRIAYLR PTQKNDGSFR YCFETGVMPD AFLIMLLRTF DLDKEVLIKQ  60
L596V      1 MIILLKEVQL EIQRRIAYLR PTQKNDGSFR YCFETGVMPD AFLIMLLRTF DLDKEVLIKQ  60

WildType  61 LTERIVSLQN EDGLWTLFDD EEHNLSATIQ AYTALLYSGY YQKNDRILRK AERYIIDSGG 120
L596A     61 LTERIVSLQN EDGLWTLFDD EEHNLSATIQ AYTALLYSGY YQKNDRILRK AERYIIDSGG 120
L596F     61 LTERIVSLQN EDGLWTLFDD EEHNLSATIQ AYTALLYSGY YQKNDRILRK AERYIIDSGG 120
L596V     61 LTERIVSLQN EDGLWTLFDD EEHNLSATIQ AYTALLYSGY YQKNDRILRK AERYIIDSGG 120

WildType 121 ISRAHFLTRW MLSVNGLYEW PKLFYLPLSL LLVPTYVPLN FYELSTYARI HFVPMMVAGN 180
L596A    121 ISRAHFLTRW MLSVNGLYEW PKLFYLPLSL LLVPTYVPLN FYELSTYARI HFVPMMVAGN 180
L596F    121 ISRAHFLTRW MLSVNGLYEW PKLFYLPLSL LLVPTYVPLN FYELSTYARI HFVPMMVAGN 180
L596V    121 ISRAHFLTRW MLSVNGLYEW PKLFYLPLSL LLVPTYVPLN FYELSTYARI HFVPMMVAGN 180

WildType 181 KKFSLTSRHT PSLSHLDVRE QKQESEETTQ ESRASIFLVD HLKQLASLPS YIHKLGYGAA 240
L596A    181 KKFSLTSRHT PSLSHLDVRE QKQESEETTQ ESRASIFLVD HLKQLASLPS YIHKLGYGAA 240
L596F    181 KKFSLTSRHT PSLSHLDVRE QKQESEETTQ ESRASIFLVD HLKQLASLPS YIHKLGYGAA 240
L596V    181 KKFSLTSRHT PSLSHLDVRE QKQESEETTQ ESRASIFLVD HLKQLASLPS YIHKLGYGAA 240

WildType 241 ERYMLERIEK DGTLYSYATS TFFMIYGLLA LGYKKDSFVI QKAIDGICSL LSTCSGHVHV 300
L596A    241 ERYMLERIEK DGTLYSYATS TFFMIYGLLA LGYKKDSFVI QKAIDGICSL LSTCSGHVHV 300
L596F    241 ERYMLERIEK DGTLYSYATS TFFMIYGLLA LGYKKDSFVI QKAIDGICSL LSTCSGHVHV 300
L596V    241 ERYMLERIEK DGTLYSYATS TFFMIYGLLA LGYKKDSFVI QKAIDGICSL LSTCSGHVHV 300

WildType 301 ENSTSTVWDT ALLSYALQEA GVPQQDPMIK GTTRYLKKRQ HTKLGDWQFH NPNTAPGGWG 360
L596A    301 ENSTSTVWDT ALLSYALQEA GVPQQDPMIK GTTRYLKKRQ HTKLGDWQFH NPNTAPGGWG 360
L596F    301 ENSTSTVWDT ALLSYALQEA GVPQQDPMIK GTTRYLKKRQ HTKLGDWQFH NPNTAPGGWG 360
L596V    301 ENSTSTVWDT ALLSYALQEA GVPQQDPMIK GTTRYLKKRQ HTKLGDWQFH NPNTAPGGWG 360

WildType 361 FSDINTNNPD LDDTSAAIRA LSRRAQTDTD YLESWQRGIN WLLSMQNKDG GFAAFEKNTD 420
L596A    361 FSDINTNNPD LDDTSAAIRA LSRRAQTDTD YLESWQRGIN WLLSMQNKDG GFAAFEKNTD 420
L596F    361 FSDINTNNPD LDDTSAAIRA LSRRAQTDTD YLESWQRGIN WLLSMQNKDG GFAAFEKNTD 420
L596V    361 FSDINTNNPD LDDTSAAIRA LSRRAQTDTD YLESWQRGIN WLLSMQNKDG GFAAFEKNTD 420

WildType 421 SILFTYLPLE NAKDAATDPA TADLTGRVLE CLGNFAGMNK SHPSIKAAVK WLFDHQLDNG 480
L596A    421 SILFTYLPLE NAKDAATDPA TADLTGRVLE CLGNFAGMNK SHPSIKAAVK WLFDHQLDNG 480
L596F    421 SILFTYLPLE NAKDAATDPA TADLTGRVLE CLGNFAGMNK SHPSIKAAVK WLFDHQLDNG 480
L596V    421 SILFTYLPLE NAKDAATDPA TADLTGRVLE CLGNFAGMNK SHPSIKAAVK WLFDHQLDNG 480

WildType 481 SWYGRWGVCY IYGTWAAITG LRAVGVSASD PRIIKAINWL KSIQQEDGGF GESCYSASLK 540
L596A    481 SWYGRWGVCY IYGTWAAITG LRAVGVSASD PRIIKAINWL KSIQQEDGGF GESCYSASLK 540
L596F    481 SWYGRWGVCY IYGTWAAITG LRAVGVSASD PRIIKAINWL KSIQQEDGGF GESCYSASLK 540
L596V    481 SWYGRWGVCY IYGTWAAITG LRAVGVSASD PRIIKAINWL KSIQQEDGGF GESCYSASLK 540

WildType 541 KYVPLSFSTP SQTAWALDAL MTICPLKDQS VEKGIKFLLN PNLTEQQTHY PTGIGLPGQF 600
L596A    541 KYVPLSFSTP SQTAWALDAL MTICPLKDQS VEKGIKFLLN PNLTEQQTHY PTGIGAPGQF 600
L596F    541 KYVPLSFSTP SQTAWALDAL MTICPLKDQS VEKGIKFLLN PNLTEQQTHY PTGIGFPGQF 600
L596V    541 KYVPLSFSTP SQTAWALDAL MTICPLKDQS VEKGIKFLLN PNLTEQQTHY PTGIGVPGQF 600

WildType 601 YIQYHSYNDI FPLLALAHYA KKHSS                                     625
L596A    601 YIQYHSYNDI FPLLALAHYA KKHSS                                     625
L596F    601 YIQYHSYNDI FPLLALAHYA KKHSS                                     625
L596V    601 YIQYHSYNDI FPLLALAHYA KKHSS                                     625
```

Figure 10-1

```
ADF38987   1 ----MIILLKE VQLEIQRRIA YLRPTQKNDG SFRYCFETGV MPDAFLIMLL RTF---DLDKE  55
AB618206   1 ----MGTLQEK VRRYQKKTIA ELKNRQNADG SWTFCFEGPI MTNSFFILLL TSLDEGENEK  57
AAU41134   1 ----------- ---------- ---------- ---------- MTDSFFILML TSL--GDQDS  18
AB007002   1 MAEQLVEAPA YARTLDRAVE YLLSCQKDEG YWWGPLLSNV TMEAEYVLLC HILD--RVDR  58

QXXXGX(W/F) motif
ADF38987  56 VLIKQLTERI VSL QNEDGLW  TLFDDE-EHN LSATIQAYTA LLYSGYYQKN DRILRKAERY 114
AB618206  58 ELISALAAGI REK QQPDGTF  INYPDETSGN ITATVQGYVG MLASGCFHRS DPHMRKAEQS 117
AAU41134  19 SLIASLAERI RSR QSEDGAF  RNHPDERAGN LTATVQGYTG MLASGLYDRK APHMQKAEAF  78
AB007002  59 DRMEKIRRYL LHE QREDGTW  ALYPGGPP-D LDTTIEAYVA LKYIGMSRDE EP-MQKALRF 116

(A/S/G)RX(H/N)XXP motif
ADF38987 115 IIDSGGISRA HFLTRWMLSV NGLYEWPKLF YLPLSLLLVP TYVPLNFYEL STY ARIHFVP 174
AB618206 118 IISHGGLRHV HFMTKWMLAV NGLYPWP-VL YLPLSLMALP PTLPVHFYQF SAY ARIHFAR 176
AAU41134  79 IKDAGGLKGV HFMTKWMLAA NGLYPWP-RA YIPLSFLLIP SYFPLHFYHF STY ARIHFVP 137
AB007002 117 IQSQGGIESS RVFTRMWLAL VGEYPWEKVP MVPPEIMFLG KRMPLNIYEF GSWARATVVA 176

ADF38987 175 MMVAGNKKFS LTSRHTPSLS HLDVREQKQE SEETTQ----E SRASIFLVDH LKQLASLPSY 231
AB618206 177 MAVTLNQRFV LKNRNIPSLR HLDPHMTKNP FTWLRSDAFE ERDLTSIWSH WNRIFHAPFA 236
AAU41134 138 MAITFNRRFS LKNNQIGSLR HLDEAMSKNP LEWLNIRAFD ERTFYSFNLQ WKQLFQWPAY 197
AB007002 177 LSIVMSRQPV FPLPER--AR VPELYETDVP PRRRGAKGGG GWIFDALDRA LHGYQKLSVH 234

ADF38987 232 -IHKLGYQAA ERYMLERIEK DGTLYSYATS TFFMIYGLLA LGYKKDSFVI QKAIDGICSL 290
AB618206 237 -FQQLGLQTA KTYMLDRIEK DGTLYSYASA TIFMVYSLLS LGVSRYSPVI KRAINGIKSL 295
AAU41134 198 -VHQLGFEAG KKYMLDRIEE DGTLYSYASA TMFMIYSLLA MGISKNAPVV KKAVSGIKSL 256
AB007002 235 PFRRAAEIRA LDWLLERQAG DGSWGGIQPP WFYALIALKI LDMTQHPAFI K-GWEGLELY 293

QXXXX(G/A/S)X(F/W/Y) motif
ADF38987 291 LSTCSG-HVH VENSTSTVWD TALLSYALQE AGVPQQDPMI KGTTRYLKKR QHTKLGDWQF 349
AB618206 296 MTKCNG-IPY LENSTSTVWD TALISYALQK NGVTETDGSI TKAAAYLLER QHTKRADWSV 354
AAU41134 257 ISSCGKEGAH LENSTSTVWD TALISYAMQE SGVPEQHSST SSAADYLLKR QHVKKADWAV 316
AB007002 294 GVELDYGGWM FQASISPVWD TGLAVLALRA AGLPADHDRL VKAGEWLLDR QITVPGDWAV 353

DXDD motif
ADF38987 350 HNPNTAPGGW GFSDINTNNP DLDD TSAAIR ALSRRAQTDT DYL-ESWQRG INWLLSMQNK 408
AB618206 355 KNPSAAPGGW GFSNINTNNP DCDD TAAVLK AIPHSYSPS- -----AWERG VSWLLSMQNN 408
AAU41134 317 SNPQAVPGGW GFSHINTNNP DLDD TAAALK AIPFQRRPD- -----AWNRG LAWLLSMQNK 370
AB007002 354 KRPNLKPGGF AFQFDNVYYP DVDD TAVVVW ALNTLRLPDE RRRRDAMTKG FRWIVGMQSS 413
```

Figure 10-2

```
           QXXXGX(F/W/Y) motif
ADF38987 409 DGGF AAFEKN TDSILFTYLP LENAKDAATD PATADLTGRV LECLGNFAGM NKSHPSIKAA 468
AB618206 409 DGGF SAFEKN VNHPLIRLLP LESAEDAAVD PSTADLTGRV LHFLGEKAGF TEKHQHIQRA 468
AAU41134 371 DGGF AAFEKD VDHPLIRNLP LESAAEAAVD PSTADLTGRV LHLLGLKGRF TDNHPAVRRA 430
AB007002 414 NGGW GAYDVD NTSDLPNHIP FCDFG-EVTD PPSEDVTAHV LECFGSFG-Y DDAWKVIRRA 471

QXXXGXW motif
ADF38987 469 VKWLFDH QLD NGSW YGRWGV CYIYGTWAAI TGLRAVGVSA SDPRIIKAIN WLKSI QQEDG 528
AB618206 469 VNWLFEH QEQ NGSW YGRWGV CYIYGTWAAL TGMHACEVDR KHPAIQKALR WLKSI QHDDG 528
AAU41134 431 LRWLDHH QKA DGSW YGRWGV CFIYGTWAAL TGMKAVGVSA NQTSVKKAIS WLKSI QREDG 490
AB007002 472 VEYLKRE QKP DGSW FGRWGV NYLYGTGAVV SALKAVGIDT REPYIQKALD WVEQH QNPDG 531

QXXXGX(F/W) motif
ADF38987 529 GF GESCYSAS LKKYVPLSFS TPSQTAWALD ALMTICPLKD RSVEKGIKFL LNPN--LTEQ 586
AB618206 529 SW GESCNSAE VKTYVPLHKG TIVQTAWALD ALLTYESSEH PSVVKGMQYL TDSSY-HGAD 587
AAU41134 491 SW GESCKSCE AKRFVPLHFG TVVQSSWALE ALLQYERPDD PQIIKGIRFL IDEHE-SSRE 549
AB007002 532 GW GEDCRSYE DPAYAGKGAS TPSQTAWALM ALIAGGRAES EAARRGVQYL VET QRPDGGW 591
                                                                   QXXXGXW motif
           GXGX(G/A/P) motif
ADF38987 587 QTHYPT GIGL PGQFYIQYHS YNDIFPLLAL AHYAKKHSS- ------                625
AB618206 588 SLAYPA GIGL PKQFYIRYHS YPYVFSLLAV GKYLNSIEKE TANET                 632
AAU41134 550 RLEYPT GIGL PNQFYIRYHS YPFVFSLLAS SAFIKKAEMR ETY--                 592
AB007002 592 DEPYYT GTGF PGDFYLGYTM YRHVFPTLAL GRYKQAIERR ------                631

ADF38987 : Bacillus megaterium DSM319_TC
AB618206 : Bacillus subtilis_TC
AAU41134 : Bacillus licheniformis DSM13(ATCC14580)_TC
AB007002 : Alicyclobacillus acidocaldarius_SHC (wildtype)
```

EFFICIENT METHOD FOR PRODUCING AMBREIN

SEQUENCE LISTING SUBMISSION VIA EFS-WEB

A computer readable text file, entitled "SequenceListing.txt," created on or about Feb. 26, 2020 with a file size of about 61 kb contains the sequence listing for this application and is hereby incorporated by reference in its entirety.

TECHNICAL FIELD

The present invention relates to a mutated tetraprenyl-β-curcumene cyclase, and a method for a method for preparing ambrein using the same. According to the present invention, ambrein can be efficiently synthesized by using squalene or 3-deoxyachilleol A as a substrate

BACKGROUND ART

Ambergris is a high grade perfume which has been used from around the seventh century, and has been also used as a Chinese medicinal drug. Ambergris is thought to be produced in sperm whales due to lithification of indigestation of foods (octopuses, squids, or the like) by gastrointestinal secretions and then excreted. The exact production mechanism, however, is unknown. The principal component of ambergris is ambrein, and it is considered that ambrein is subject to oxidative decomposition by sunlight and oxygen, while the ambergris floats on the ocean's surface, thereby producing compounds having a variety of fragrances.

Although ambrein, the principal component of ambergris, is used as perfume or in pharmaceuticals, it is impossible to obtain a large quantity of ambrein is naturally produced. A variety of organic synthesis methods have thus been proposed.

For example, as a method of producing (+)-ambrein easily, efficiently and inexpensively. Patent literature 1 discloses a method comprising a step of producing a new sulfonic acid derivative from ambrenolide and coupling with an optically active γ-cyclogeranyl halide.

Non-patent literature 1 discloses a method of obtaining ambrein by convergent synthesis using a Julia coupling reaction between 2-(1R,2R,4aS,8aS)-2-(methoxymethoxy)-2,5,5,8a-tetramethyl decahydronaphthalene-1-yl) acetaldehyde synthesized from (±)(5,5,8a-trimethyloctahydro-1H-spiro[naphthalene-2,2'-oxirane]-1-yl)methanol and 5-((4-((S)-2,2-dimethyl-6-methylenecyclohexyl)butane-2-yl)sulfonyl)-1-phenyl-1H-tetrazole synthesized from (±)methyl 6-hydroxy-2,2-dimethyl cyclohexanecarboxylate.

However, since conventional organic synthesis methods of ambrein involve many synthesis stages, the reaction systems are complex, and therefore commercialization thereof has been unsuccessful.

CITATION LIST

Patent Literature

[Patent literature 1] Japanese Unexamined Patent Publication (Kokai) No 10-236996
[Patent literature 2] WO 2015/033746

Non-Patent Literature

[Non-patent literature 1] Tetrahedron Asymmetry, (2006) Vol. 17, pp. 30373rd045
[Non-patent literature 2] Biosci. Biotechnol. Biochem., (1999) Vol. 63, pp. 2189-2198
[Non-patent literature 3] Biosci. Biotechnol. Biochem., (2001) Vol. 65, pp. 2233-2242
[Non-patent literature 4] Biosci. Biotechnol. Biochem., (2002) Vol. 66, pp. 1660-167th0
[Non-patent literature 5] J. Am. Chem. Soc., (2011) Vol. 133, pp. 17540-17543
[Non-patent literature 6] J. Am. Chem. Soc., (2013) Vol. 135, pp. 18335-18338

SUMMARY OF INVENTION

Technical Problem

A method in which 3-deoxyachilleol A which is a monocyclic triterpene is obtained from squalene by using a mutated enzyme (D377C, D377N, Y420H, Y420W, or the like) of a squalene-hopene cyclase is also known (Non-patent literatures 2-4).

The present inventors found that ambrein can be produced by reacting a mutated squalene-hopene cyclase capable of producing 3-deoxyachilleol A from squalene with squalene to obtain 3-deoxyachilleol A, and further reacting tetraprenyl-β-curcumene cyclase therewith to produce ambrein (Patent literature 2).

However, there are a problem that a by-product is formed in the 2nd step reaction, (i.e., the reaction converting 3-deoxyachilleol A to ambrein), and a problem of difficulty in scaling up. Further, the method disclosed in Patent literature 2 is a multi-step reaction. Furthermore, there is also room for improvement in yield.

Accordingly, the object of the present invention is to provide an ambrein-preparation method capable of easily and efficiently obtaining ambrein.

Solution to Problem

The present inventors conducted intensive studies into a method for easily preparing ambrein, and as a result, surprisingly found that a mutated tetraprenyl-β-curcumene cyclase having a few specific mutations has an activity to produce ambrein from squalene. In addition to the above mutations, the present inventors have found that a mutated tetraprenyl-β-curcumene cyclase having a further mutation has an activity of more efficiently producing ambrain from squalene. Further, the present inventors have found that a mutated tetraprenyl-β-curcumene cyclase with a specific mutation has the activity of efficiently producing ambrain from 3-deoxyachilleol A.

The present invention is based on the above findings.
Namely, the present invention relates to:
[1] a mutated tetraprenyl-β-curcumene cyclase wherein (1) a 4th amino acid residue of a DXDD motif, aspartic acid, is substituted with an amino acid other than aspartic acid, and (2) an amino acid adjacent to the N-terminus of an (A/S/G)RX(H/N)XXP motif is substituted with an amino acid other than tyrosine, or a 4th amino acid of the GXGX(G/A/P) motif is substituted with an amino acid other than leucine, (a) having a QXXXGX(W/F) motif at a position separated by 100 amino acid residues or more on the N-terminal side, an (A/S/G)RX(H/N)XXP motif at a position separated by 180 to 250 amino acid residues on the N-terminal side, a QXXXX(G/A/S)X(F/W/Y) motif at a position separated by 10 to 50 amino acids residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, a QXXXGX(F/W) motif at a position separated by 120 to 170 amino acid residues on the C-terminal side, and a GXGX(G/A/P) motif at a position separated by 180 to 250 amino acid residues on the C-terminal side, with respect to the DXDD motif, (b) having 40% or more identity with the amino acid sequence of SEQ ID NO: 1, and (c) exhibiting ambrein production activity using squalene as a substrate,

[2] the mutated tetraprenyl-β-curcumene cyclase of item [1], not having a QXXXGXW motif at a position separated by 170 amino acid residues or more on the C-terminal side, with respect to the DXDD motif,

[3] the mutated tetraprenyl-β-curcumene cyclase of item [1] or [2], wherein a polypeptide constituting the mutated tetraprenyl-β-curcumene cyclase is (1) a polypeptide wherein aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, (2) a polypeptide wherein one or plural amino acids are deleted, substituted, inserted and/or added in the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, (3) a polypeptide having 40% or more identity with the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, (4) a polypeptide comprising the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, (5) a polypeptide comprising the amino acid sequence wherein one or plural amino acids are deleted, substituted, inserted and/or added in the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, or (6) a polypeptide comprising an amino acid sequence having 40% or more identity with the amino acids sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate,

[4] the mutated tetraprenyl-β-curcumene cyclase of any one of items [1] to [3], wherein the 4th amino acid residue of a DXDD motif is substituted with cysteine or glycine from aspartic acid, and the amino acid adjacent to the N-terminus of an (A/S/G)RX(H/N)XXP motif is substituted with alanine or glycine from tyrosine, or the 4th amino acid of the GXGX(G/A/P) motif is substituted with alanine or phenylalanine from leucine,

[5] a mutated tetraprenyl-β-curcumene cyclase having DXDD motif wherein a 4th amino acid of the GXGX(G/A/P) motif is an amino acid other than leucine, glycine or proline, (a) having a QXXXGX(W/F) motif at a position separated by 100 amino acid residues or more on the N-terminal side, a QXXXX(G/A/S)X(F/W/Y) motif at a position separated by 10 to 50 amino acids residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, a QXXXGX(F/W) motif at a position separated by 120 to 170 amino acid residues on the C-terminal side, and a GXGX(G/A/P) motif at a position separated by 180 to 250 amino acid residues on the C-terminal side, with respect to the DXDD motif, (b) having 40% or more identity with the amino acid sequence of SEQ ID NO: 1, and (c) exhibiting ambrein production activity using 3-deoxyachilleol A as a substrate,

[6] the mutated tetraprenyl-β-curcumene cyclase of item [5], not having a QXXXGXW motif at a position separated by 170 amino acid residues or more on the C-terminal side, with respect to the DXDD motif,

[7] the mutated tetraprenyl-β-curcumene cyclase of item [5] or [6], wherein a polypeptide constituting the mutated tetraprenyl-β-curcumene cyclase is (1) a polypeptide wherein leucine at position 596 from the N-terminal in the amino acid sequence of SEQ ID NO: 1 is substituted with an amino acid other than leucine, (2) a polypeptide wherein one or plural amino acids are deleted, substituted, inserted and/or added in the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, (3) a polypeptide having 40% or more identity with the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, (4) a polypeptide comprising the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, (5) a polypeptide comprising the amino acid sequence wherein one or plural amino acids are deleted, substituted, inserted and/or added in the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, or (6) a polypeptide comprising an amino acid sequence having 40% or more identity with the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate,

[8] the mutated tetraprenyl-β-curcumene cyclase of any one of items [5] to [7], wherein the 4th amino acid of the GXGX(G/A/P) motif is alanine or phenylalanine,

[9] a polynucleotide encoding the mutated tetraprenyl-β-curcumene cyclase of any one of items [1] to [8],

[10] a microorganism having the polynucleotide of item [9],

[11] a vector comprising a DNA having the polynucleotide of item [9],

[12] a transformant having the vector of item [11],

[13] a method for preparing ambrein characterized by bringing into contact the mutated tetraprenyl-β-curcumene cyclase of any one of items [1] to [4] with squalene, to obtain ambrein,

[14] a method for preparing ambrein characterized by bringing into contact the mutated tetraprenyl-β-curcumene cyclase of any one of items [5] to [8] with 3-deoxyachilleol A, to obtain ambrein, and

[15] a method for preparing ambrein characterized by culturing the microorganism according claim 10, or the transformant of item [12].

Advantageous Effects of Invention

According to an embodiment of the mutated tetraprenyl-β-curcumene cyclase of the present invention, ambrein can be synthesized in one step using squalene as a substrate, without a concomitant use of a mutated squalene-hopene cyclase. Further, an ambrein can be efficiently prepared from a carbon source contained in a culture solution by microbial fermentation.

The mutated tetraprenyl-β-curcumene cyclase used in the present invention can produce 3-deoxyachilleol A from squalene. Further, the mutated tetraprenyl-β-curcumene cyclase used in the present invention can produce ambrein from the bicyclic triterpene (8α-hydroxypolypoda-13,17,21-triene).

The mutated tetraprenyl-β-curcumene cyclase used in the present invention can exhibit the above-mentioned effect efficiently, when compared with a tetraprenyl-β-curcumene cyclase, wherein the 4th amino acid residue of the DXDD motif, aspartate, is only substituted with an amino acid other than aspartate.

According to another embodiment of the mutated tetraprenyl-β-curcumene cyclase of the present invention, ambrein can be efficiently produced from 3-deoxyachilleol A.

BRIEF DESCRIPTION OF THE DRAWINGS

FIG. 8 is a chart showing the amino acid sequences of the wild type tetraprenyl-β- curcumene cyclase (WildType; SEQ ID NO:1), the mutated tetraprenyl-β-curcumene cyclase wherein aspartic acid at position 373 is substituted with cysteine, and tyrosine at position 167 is substituted with alanine (Y167A/D373C; SEQ ID NO:5), and the mutated tetraprenyl-β-curcumene cyclase wherein aspartic acid at position 373 is substituted with cysteine, and leucine at position 596 is substituted with alanine (D373C/L596A; SEQ ID NO:6).

FIG. 9 is a chart showing the amino acid sequences of the wild type tetraprenyl-β- curcumene cyclase (WildType; SEQ ID NO:1), the mutated tetraprenyl-β-curcumene cyclase wherein leucine at position 596 is substituted with alanine (L596A; SEQ ID NO:9), the mutated tetraprenyl-β-curcumene cyclase wherein leucine at position 596 is substituted with phenylalanine (L596F; SEQ ID NO:10), and the mutated tetraprenyl-β-curcumene cyclase wherein leucine at position 596 is substituted with valine (L596V; SEQ ID NO:13).

FIG. 10 is a chart showing an alignment of amino acid sequences of the tetraprenyl-β- curcumene cyclase of Bacillus megaterium (ADF38987; SEQ ID NO:1), Bacillus subtilis (AB618206;

Figure 1:
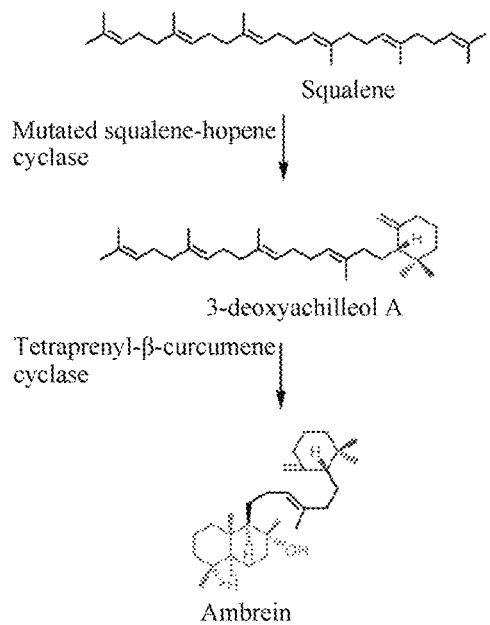
FIG. 1 is a diagram showing a conventional ambrein synthesis pathway using squalene as a substrate, wherein the mutated squalene-hopene cyclase and tetraprenyl-β-curcumene cyclase (A), and a diagram showing an ambrein synthesis pathway using 3-deoxyachilleol A as a substrate, wherein the mutated tetraprenyl-β-curcumene cyclase of the present invention (A).
Figure 1:
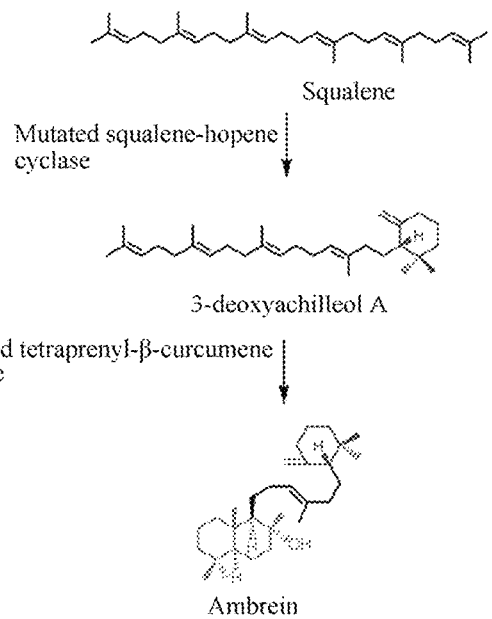

SEQ ID NO:2), and Bacillus licheniformis (AAU41134; SEQ ID NO:3), and amino acid sequence of the squalene-hopene cyclase of Alicyclobacillus acidocaldarius (AB007002; SEQ ID NO:4).

DESCRIPTION OF EMBODIMENTS

Tetraprenyl-β-curcumene Cyclase

The wild type tetraprenyl-β-curcumene cyclase (hereinafter sometimes referred to as a TC) can produce ambrein by using 3-deoxyachilleol A, which comprises a monocycle at one end, as a substrate. That is, when 3-deoxyachilleol A is utilized as a substrate, the tetraprenyl-β-curcumene cyclase selectively forms a ring on the end of the 3-deoxyachilleol A on which a ring has not formed to produce a compound which is cyclized at both ends.

Further, the tetraprenyl-β-curcumene cyclase can produce bicyclic 8α-hydroxypolypoda-13, 17, 21-triene using squalene as a substrate (Non-patent literature 5). Furthermore, the tetraprenyl-β-curcumene cyclase selectively forms a ring on the end of the bicyclic 8α-hydroxypolypoda-13, 17, 21-triene on which a ring has not been formed to produce a onoceranoxide and 14β-hydroxyonocera-8(26)-en which are cyclized at both ends (Non-patent literature 6).

That is to say, tetraprenyl-β-curcumene cyclase, which is classified as belonging to EC 4.2.1.129, is an enzyme capable of catalyzing a reaction which produces baciterpenol A from water and tetraprenyl-β-curcumene or a reaction which produces 8α-hydroxypolypoda-13, 17, 21-triene from squalene.

For example, bacteria such as *Bacillus, Brevibacillus, Paenibacilus*, or *Geobacillus* has the tetraprenyl-β-curcumene cyclase. As the *Bacillus* bacterium, there may be mentioned *Bacillus subtilis, Bacillus megaterium*, or *Bacillus licheniformis*. The tetraprenyl-β-curcumene cyclase has a QXXXGX(W/F) motif at a position separated by 100 amino acid residues or more on the N-terminal side, a QXXXX (G/A/S)X(F/W/Y) motif at a position separated by 10 to 50 amino acid residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, and a QXXXGX(F/W) motif at a position separated by 120 to 170 amino acid residues on the C-terminal side, with respect to the DXDD motif. The squalene-hopene cyclase also has the above motifs, and further has a QXXXGXW motif at a position separated by 170 amino acid residues or more on the C-terminal side, with respect to the DXDD motif. On the other hand, the tetraprenyl-β-curcumene cyclase does not have the QXXXGXW motif. Furhtermore, the tetraprenyl-β-curcumene cyclase preferably has a (A/S/G)RX(H/N)XXP motif at a position separated by 180 to 250 amino acid residues on the N-terminal side, with respect to the DXDD motif, but the squalene-hopene cyclase does not have the (A/S/G)RX(H/N)XXP motif. Further, squalene-hopene cyclase has a GXGFP motif on the C-terminal side of the QXXXGXW motif, and is characterized in that the 4th amino acid of the DXDD motif is phenylalanine (F). The tetraprenyl-β-curcumene cyclase also has a GXGX(G/A/P) motif similar to the GXGFP motif. However, the 4th amino acid is not phenylalanine, but is basically leucine (L).

[1] Mutated tetraprenyl-β-curcumene cyclase

First Embodiment

In the first embodiment of the mutated tetraprenyl-β-curcumene cyclase of the present invention, (1) a 4th amino acid residue of a DXDD motif, aspartic acid, is substituted with an amino acid other than aspartic acid, and (2) an amino acid adjacent to the N-terminus of an (A/S/G)RX(H/N)XXP motif is substituted with an amino acid other than tyrosine, or a 4th amino acid of the GXGX(G/A/P) motif is substituted with an amino acid other than leucine, and the mutated tetraprenyl-β-curcumene cyclase has (a) a QXXXGX(W/F) motif at a position separated by 100 amino acid residues or more on the N-terminal side, an (A/S/G)RX(H/N)XXP motif at a position separated by 180 to 250 amino acid residues on the N-terminal side, a QXXXX(G/A/S)X(F/W/Y) motif at a position separated by 10 to 50 amino acids residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, a QXXXGX (F/W) motif at a position separated by 120 to 170 amino acid residues on the C-terminal side, and a GXGX(G/A/P) motif at a position separated by 180 to 250 amino acid residues on the C-terminal side, with respect to the DXDD motif, and has (b) 40% or more identity with the amino acid sequence of SEQ ID NO: 1, and exhibits (c) ambrein production activity using squalene as a substrate.

Alphabets defining each motif or sequence mean one letter amino acid codes, and the character "X" means an arbitrary amino acid. That is to say, in the case of the QXXXGX (W/F) motif, glutamine (Q), any three amino acids (X), glycine (G), any amino acid (X), any one of tryptophan (W) or phenylalanine (F) are arranged from the N terminus to the C terminus. In addition, the wording "having QXXXGX(W/F) motif at a position separated by 100 amino acid residues or more on the N-terminal side with respect to the DXDD motif" means that there are 100 amino acid residues or more between the DXDD motif and the QXXXGX (W/F) motif. Identification of other motifs is similar. Hereinafter, the same applies unless otherwise noted.

Further, the 4th amino acid residue of a GXGX(G/A/P) motif means the 4th amino acid counted from the N-terminal side, and the same applies to other sequences. Hereinafter, the same applies unless otherwise noted.

Amino acid sequence identity is expressed as a percentage by aligning with appropriate gaps so that the amino acid residues of the sequences being compared match, and by dividing the number of matched amino acid residues by the total number of amino acid residues.

Identity can be calculated using well-known programs (e.g. BLAST, FASTA, CLUSTAL W, etc.).

As the preferable embodiment of the first embodiment of the mutated tetraprenyl-β-curcumene cyclase of the present invention, a polypeptide constituting the mutated tetraprenyl-β-curcumene cyclase is (1) a polypeptide wherein aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, (2) a polypeptide wherein one or plural amino acids are deleted, substituted, inserted and/or added in the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, (3) a polypeptide having 40% or more identity with the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, (4) a polypeptide comprising the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, (5) a polypeptide comprising the amino acid sequence wherein one or plural amino acids are deleted, substituted, inserted and/or added in the amino acid sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate, or (6) a polypeptide comprising an amino acid sequence having 40% or more identity with the amino acids sequence in which aspartic acid at position 373 from the N-terminal in the amino acid sequence of SEQ ID NO: 1 is substituted with an amino acid other than aspartic acid; and tyrosine at position 167 from the N-terminal in the amino acid sequence of SEQ ID NO: 1 is substituted with an amino acid other than tyrosine, or leucine at position 596 from the N-terminal in the amino acid sequence of SEQ ID NO: 1 is substituted with an amino acid other than leucine, and exhibiting ambrein production activity using squalene as a substrate.

Further, according to a most preferable embodiment of the mutated tetraprenyl-β-curcumene cyclase of the present invention, the polypeptide constituting the mutated tetraprenyl-β-curcumene cyclase includes a polypeptide consisting of the amino acid sequence of SEQ ID NO: 5 or 6 which is derived from *Bacillus megaterium*. In this mutated tetraprenyl-β-curcumene cyclase, a 4th amino acid residue of a DXDD motif, aspartic acid, is substituted with cysteine, and an amino acid adjacent to the N-terminus of an (A/S/G)RX(H/N)XXP motif is substituted with alanine, or a 4th amino acid of the GXGX(G/A/P) motif is substituted with alanine.

(Substitution of 4th Amino Acid Residue of DXDD Motif)

In the mutated tetraprenyl-β-curcumene cyclase (hereinafter sometimes referred to as a mutated TC) of the present invention, the 4th amino acid residue of the DXDD motif is substituted with an amino acid other than aspartic acid. The amino acid other than aspartic acid is not limited, as long as the effect of the present invention can be achieved, but includes alanine, cysteine, glutamic acid, phenylalanine, glycine, histidine, isoleucine, lysine, leucine, methionine, asparagine, proline, glutamine, arginine, serine, threonine, valine, tryptophan, or tyrosine. However, it is preferably cysteine or glycine, more preferably cysteine.

By substituting the 4th amino acid residue of the DXDD motif with the amino acid other than aspartic acid (particularly cysteine or glycine), the mutated tetraprenyl-β-curcumene cyclase of the present invention can produce 3-deoxyachilleol A from squalene, and can produce ambrein from 8α-hydroxypolypoda-13,17,21-triene.

For example, the DXDD motif is located at positions 370th to 373 from the N-terminal side of the amino acid sequence of SEQ ID NO:1 of the tetraprenyl-β-curcumene cyclase of *Bacillus megaterium*. Further, it is located at positions 375th to 378th from the N-terminal side of the amino acid sequence of SEQ ID NO:2 of the tetraprenyl-β-curcumene cyclase of *Bacillus subtilis*. The above aspartic acid of the DXDD motif is extremely highly conserved, and generally, the 4th amino acid residue from the N-terminal side thereof is aspartic acid (FIG. 10).

(Substitution of Amino Acid Residue Adjacent to N-Terminus of (A/S/G)RX(H/N)XXP Motif)

In the mutated TC of the present invention, the amino acid residue adjacent to the N-terminus of an (A/S/G)RX(H/N)XXP motif is substituted with an amino acid other than tyrosine. The amino acid other than tyrosine is not limited, as long as the effect of the present invention can be achieved, but includes alanine, cysteine, glutamic acid, phenylalanine, glycine, histidine, isoleucine, lysine, leucine, methionine, asparagine, proline, glutamine, arginine, serine, threonine, valine, tryptophan, or aspartic acid. However, it is preferably hydrophobic amino acids (glycine, alanine, valine, leucine, isoleucine, methionine, proline, phenylalanine, and tryptophan). In particular, it is preferably alanine or glycine, more preferably alanine.

By substituting the amino acid residue adjacent to the N-terminus of an (A/S/G)RX(H/N)XXP motif with the amino acid other than tyrosine (particularly alanine or glycine), the mutated tetraprenyl-β-curcumene cyclase of the present invention has improved functions of producing 3-deoxyachilleol A from squalene and producing ambrein from 8α-hydroxypolypoda-13,17,21-triene.

For example, the (A/S/G)RX(H/N)XXP motif is located at positions 168 to 174 from the N-terminal side of the amino acid sequence of SEQ ID NO:1 of the tetraprenyl-β-curcumene cyclase of *Bacillus megaterium*. Further, it is located at positions 170 to 176 from the N-terminal side of the amino acid sequence of SEQ ID NO:2 of the tetraprenyl-β-curcumene cyclase of *Bacillus subtilis*. The above amino acid residue adjacent to the N-terminus of the (A/S/G)RX(H/N)XXP motif is extremely highly conserved, and it is basically tyrosine (FIG. 10) in the wild type. In the present invention, it has been found that, the tetraprenyl-β-curcumene cyclase has improved the ambrein production activity using squalene as a substrate, by mutating this specific amino acid with high conservation.

(Substitution of 4th Amino Acid Residue of GXGX(G/A/P) Motif)

In the mutated TC of the present invention, the 4th amino acid residue of the GXGX(G/A/P) motif is substituted with an amino acid other than leucine. The amino acid other than leucine is not limited, as long as the effect of the present invention can be achieved, but includes alanine, cysteine, glutamic acid, phenylalanine, glycine, histidine, isoleucine, lysine, methionine, asparagine, proline, glutamine, arginine, serine, threonine, valine, tryptophan, tyrosine or aspartic acid. However, it is preferably alanine, phenylalanine, valine, methionine, isoleucine, or tryptophan. In particular, it is preferably alanine or phenylalanine, more preferably alanine.

By substituting the amino acid residue of the 4th amino acid residue of the GXGX(G/A/P) motif with the amino acid other than leucine (particularly alanine or phenylalanine), the mutated tetraprenyl-β-curcumene cyclase of the present invention has improved functions of producing 3-deoxyachilleol A from squalene and producing ambrein from 8α-hydroxypolypoda-13,17,21-triene.

For example, the GXGX(G/A/P) motif is located at positions 593 to 597 from the N-terminal side of the amino acid sequence of SEQ ID NO:1 of the tetraprenyl-β-curcumene cyclase of *Bacillus megaterium*. Further, it is located at positions 594 to 598 from the N-terminal side of the amino acid sequence of SEQ ID NO:2 of the tetraprenyl-β-curcumene cyclase of *Bacillus subtilis*. The 4th amino acid residue of the motif is leucine as far as the inventors know, in the wild type whose function is confirmed (FIG. 10), In the present invention, it has been found that, the tetraprenyl-β-curcumene cyclase has improved the ambrein production activity using squalene as a substrate, by mutating this leucin.

FIG. 8 shows amino acid sequences of wild type tetraprenyl-β-curcumene cyclase of *Bacillus megaterium*, the mutated tetraprenyl-β-curcumene cyclase in which aspartic acid at position 373 is substituted with cysteine, and tyrosine at position 167 is substituted with alanine, and the mutated tetraprenyl-β-curcumene cyclase in which aspartic acid at position 373 is substituted with cysteine, and leucine at position 596 is substituted with alanine.

Origin of the mutated tetraprenyl-β-curcumene cyclase of the present invention is not particularly limited, and all tetraprenyl-β-curcumene cyclases can be used. That is, the mutated tetraprenyl-β-curcumene cyclase wherein the 4th amino acid of the DXDD motif, aspartic acid, is substituted with an amino acid other than aspartic acid (preferably cysteine or glycine), and the 4th amino acid of the GXGX (G/A/P) motif is substituted with an amino acid other than leucine (preferably alanine or phenylalanine) or the amino acid adjacent to the N-terminus of a (A/S/G)RX(H/N)XXP motif is substituted with an amino acid other than tyrosine (preferably alanine or glycine), can exhibit the effect of the present invention. More specifically, the mutated tetraprenyl-β-curcumene cyclase wherein it has a QXXXGX(W/F) motif at a position separated by 100 amino acid residues or more on the N-terminal side, an (A/S/G)RX(H/N)XXP motif at a position separated by 180 to 250 amino acid residues or more on the N-terminal side, a QXXXX(G/A/S)X(F/W/Y) motif at a position separated by 10 to 50 amino acids residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, a QXXXGX(F/W) motif at a position separated by 120 to 170 amino acid residues on the C-terminal side, and a GXGX(G/A/P) motif at a position separated by 180 to 250 amino acid residues on the C-terminal side, with respect to the DXDD motif; and the 4th amino acid of the DXDD motif, aspartic acid, is substituted with an amino acid other than aspartic acid (preferably cysteine or glycine), and the 4th amino acid of the GXGX(G/A/P) motif is substituted with an amino acid other than leucine (preferably alanine or phenylalanine) or the amino acid adjacent to the N-terminus of a (A/S/G)RX(H/N)XXP motif is substituted with an amino acid other than tyrosine (preferably alanine or glycine), can exhibit the effect of the present invention. Preferably, the mutated tetraprenyl-β-curcumene cyclase of the present invention does not have the QXXXGXW motif at a position separated by 170 amino acid residues or more on the C-terminal side, with respect to the DXDD motif. For example, the amino acid sequence identity of the polypeptides between *Bacillus subtilis* and *Bacillus megaterium* is about 50%. However, both enzymes have the feature of the present invention, and thus can produce 3-deoxychilleol A from squalene and produce ambrein from 8α-hydroxypolypoda-13, 17, 21-triene. In connection to this, the amino acid sequence of tetraprenyl-β-curcumene cyclase of *Bacillus megaterium* is shown in SEQ ID NO:1, and the amino acid sequence of tetraprenyl-β-curcumene cyclase of *Bacillus subtilis* shown in SEQ ID NO:2.

Second Embodiment

The mutated tetraprenyl-β-curcumene cyclase of a second embodiment of the present invention has the DXDD motif, and a 4th amino acid of the GXGX(G/A/P) motif is substituted with an amino acid other than n leucine. Further, the mutated tetraprenyl-β-curcumene cyclase has (a) a QXXXGX(W/F) motif at a position separated by 100 amino acid residues or more on the N-terminal side, a QXXXX (G/A/S)X(F/W/Y) motif at a position separated by 10 to 50 amino acids residues on the N-terminal side, a QXXXGX (F/W/Y) motif at a position separated by 20 to 50 amino acid residues on the C-terminal side, a QXXXGXW motif at a position separated by 50 to 120 amino acid residues on the C-terminal side, a QXXXGX(F/W) motif at a position separated by 120 to 170 amino acid residues on the C-terminal side, and a GXGX(G/A/P) motif at a position separated by 180 to 250 amino acid residues on the C-terminal side, with respect to the DXDD motif, and has (b) 40% or more identity with the amino acid sequence of SEQ ID NO: 1, and exhibits (c) ambrein production activity using 3-deoxyachilleol A as a substrate The definition of alphabetsof each motif or sequence is the same as in the first embodiment As the preferable embodiment of the second embodiment of the mutated tetraprenyl-β-curcumene cyclase of the present invention, a polypeptide constituting the mutated tetraprenyl-β-curcumene cyclase is (1) a polypeptide wherein leucine at position 596 from the N-terminal in the amino acid sequence of SEQ ID NO: 1 is substituted with an amino acid other than leucine, (2) a polypeptide wherein one or plural amino acids are deleted, substituted, inserted and/or added in the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, (3) a polypeptide having 40% or more identity with the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, (4) a polypeptide comprising the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, (5) a polypeptide comprising the amino acid sequence wherein one or plural amino acids are deleted, substituted, inserted and/or added in the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate, or (6) a polypeptide comprising an amino acid sequence having 40% or more identity with the amino acid sequence in which leucine at position 596 from the N-terminal in the amino acid sequence of SEQ ID NO: 1 is substituted with an amino acid other than leucine, and exhibiting ambrein production activity using 3-deoxyachilleol A as a substrate.

Further, according to a most preferable second embodiment of the mutated tetraprenyl-β-curcumene cyclase of t the present invention, the polypeptide constituting the mutated tetraprenyl-β-curcumene cyclase includes a polypeptide consisting of the amino acid sequence of SEQ ID NO: 9, 10 or 13, which is derived from *Bacillus megaterium*. In this mutated tetraprenyl-β-curcumene cyclase, a 4th amino acid of a GXGX(G/A/P) motif is substituted with alanine, phenylalanine, or valine.

(Substitution of 4th Amino Acid Residue of GXGX(G/A/P) Motif)

In the mutated TC of the present invention, the 4th amino acid residue of the GXGX(G/A/P) motif is an amino acid other than leucine, glycine, and proline. The 4th amino acid is not limited, as long as the effect of the present invention can be achieved, but includes alanine, cysteine, glutamic acid, phenylalanine, histidine, isoleucine, lysine, methionine, asparagine, glutamine, arginine, serine, threonine, tryptophan, tyrosine or aspartic acid. However, it preferably includes alanine, phenylalanine, methionine, isoleucine, or tryptophan. In particular, it is preferably alanine or phenylalanine, more preferably alanine.

By substituting the amino acid residue of the 4th amino acid residue of the GXGX(G/A/P) motif with the amino acid other than leucine (particularly alanine or phenylalanine), the mutated tetraprenyl-β-curcumene cyclase of the present invention has improved function of producing ambrein from 3-deoxyachilleol A.

For example, the GXGX(G/A/P) motif is located at positions 593rd to 597th from the N-terminal side of the amino acid sequence of SEQ ID NO:1 of the tetraprenyl-β-curcumene cyclase of *Bacillus megaterium*. Further, it is located at positions 594th to 598th from the N-terminal side of the amino acid sequence of SEQ ID NO:2 of the tetraprenyl-β-curcumene cyclase of *Bacillus subtilis*. The 4th amino acid residue of the motif is leucine as far as the inventors know, in the wild type whose function is confirmed. In the present invention, it has been found that, the tetraprenyl-β-curcumene cyclase can efficiently produce ambrein from 3-deoxyachilleol A, by mutating the leucine to an amino acid other than leucine, glycine, and proline.

Figure 7:
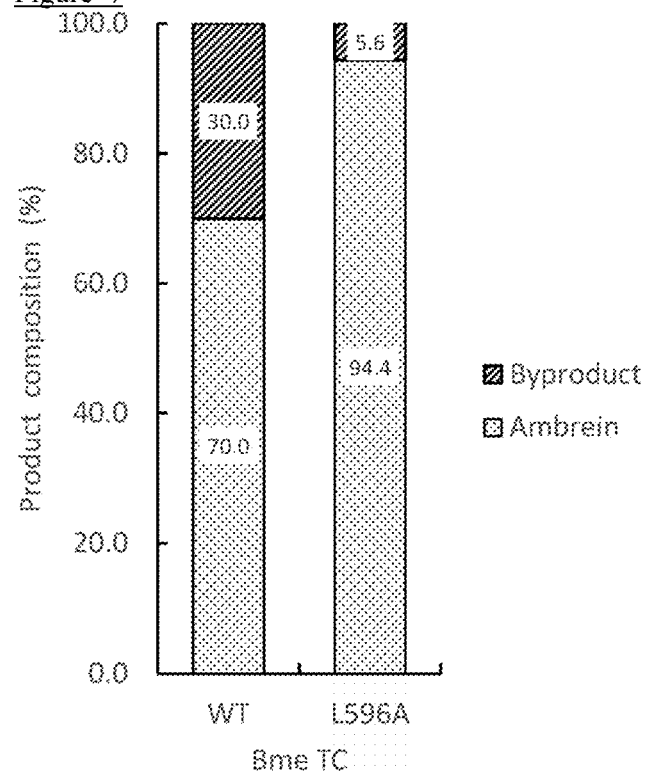
FIG. 7 is a graph showing the rate of ambrein and the other reaction products (by-products) in the enzymatic reaction using 3-deoxyachilleol A as a substrate by using wild type (Comparative Example 5), L596A mutant (Example 5).

FIG. 7 shows amino acid sequences of wild type tetraprenyl-β-curcumene cyclase of *Bacillus megaterium*, and the mutated tetraprenyl-β-curcumene cyclase in which leucine at position 596 is substituted with alanine or phenylalanine.

Origin of the mutated tetraprenyl-β-curcumene cyclase of the present invention is not particularly limited, and all tetraprenyl-β-curcumene cyclases can be used. That is, the mutated tetraprenyl-β-curcumene cyclase wherein the 4th amino acid of the GXGX(G/A/P) motif is substituted with an amino acid other than tyrosine (preferably alanine or phenylalanine), can exhibit the effect of the present invention. More specifically, the mutated tetraprenyl-β-curcumene cyclase wherein it has a QXXXGX(W/F) motif at a position separated by 100 amino acid residues or more on the N-terminal side, a QXXXX(G/A/S)X(F/W/Y) motif at a position separated by 10 to 50 amino acids residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, a QXXXGX (F/W) motif at a position separated by 120 to 170 amino acid residues on the C-terminal side, and a GXGX(G/A/P) motif at a position separated by 180 to 250 amino acid residues on the C-terminal side, with respect to the DXDD motif; and the 4th amino acid of the GXGX(G/A/P) motif is substituted with an amino acid other than tyrosine (preferably alanine or phenylalanine), can exhibit the effect of the present invention. Preferably, the mutated tetraprenyl-β-curcumene cyclase of the present invention does not have the QXXXGXW motif at a position separated by 170 amino acid residues or more on the C-terminal side, with respect to the DXDD motif. For example, the amino acid sequence identity of the polypeptides between *Bacillus subtilis* and *Bacillus megaterium* is about 50%. However, both enzymes have the feature of the present invention, and thus can improve the production efficiency of ambrein from 3-deoxyachilleol A. In connection to this, the amino acid sequence of tetraprenyl-β-curcumene cyclase of *Bacillus megaterium* is shown in SEQ ID NO:1, and the amino acid sequence of tetraprenyl-β-curcumene cyclase of *Bacillus subtilis* shown in SEQ ID NO:2. Furthermore, the mutated tetraprenyl-β-curcumene cyclase of a second embodiment of the present invention preferably has a (A/S/G)RX(H/N)XXP motif at a position separated by 180 to 250 amino acid residues on the N-terminal side, with respect to the DXDD motif, FIG. 10 shows an alignment of amino acid sequences of the tetraprenyl-β-curcumene cyclase of *Bacillus megaterium* (SEQ ID NO: 1), *Bacillus subtilis* (SEQ ID NO: 2), and *Bacillus licheniformis* (SEQ ID NO: 3), and amino acid sequence of the squalene-hopene cyclase of *Alicyclobacillus acidocaldarius* (SEQ ID NO: 4). The first and second embodiments of the mutated tetraprenyl-β-curcumene cyclase of the present invention has a QXXXGX(W/F) motif at a position separated by 100 amino acid residues or more on the N-terminal side, with respect to the DXDD motif, preferably has two motif A at a position separated by 100 amino acid residues or more on the N-terminal side, with respect to the DXDD motif.

As shown in FIG. 1, when producing ambrein from squalene, conventionally, squalene is converted to 3-deoxyachilleol A by a mutated squalene-hopene cyclase (hereinafter sometimes referred to as mutated SHC), and then 3-deoxyachilleol A is converted to ambrein by wild type tetraprenyl-β-curcumene cyclase, to produce ambrein (Patent literature 2). As shown in FIG. 1(B), the efficiency of converting 3-deoxyachilleol A to ambrein was significantly improved by using the mutated tetraprenyl-β-curcumene cyclase of the second embodiment of the present invention.

Figure 2:
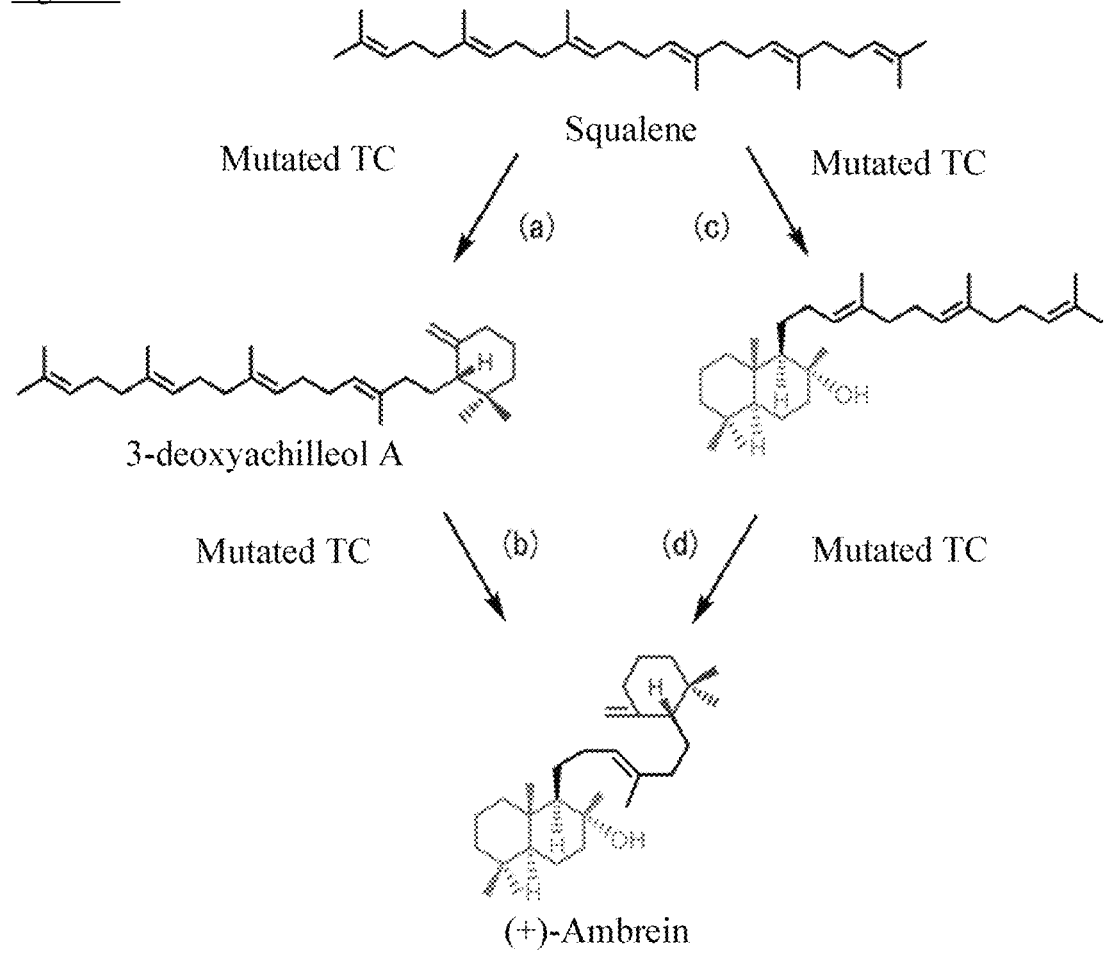
FIG. 2 is a diagram showing two pathways for preparing ambrein from squalene, using the mutated tetraprenyl-β-curcumene cyclase of the present invention.

When ambrein is produced from squalene by using the mutated tetraprenyl-β-curcumene cyclase of the second embodiment of the present invention, it is produced through a pathway with monocyclic 3-deoxyachilleol A as an intermediate (hereinafter sometimes referred to as a monocyclic pathway) and a pathway with 8α-hydroxypolypoda-13, 17, 21-triene as an intermediate (hereinafter referred to as a bicyclic pathway), as shown in FIG. 2.

(Monocyclic Pathway)

In the monocyclic pathway, the monocyclic 3-deoxyachilleol A is produced from squalene by the mutated TC, and then ambrein is produced from 3-deoxyachilleol A by the mutated TC. The conventional wild type TC can convert 3-deoxyachilleol A to ambrein, but cannot convert squalene to monocyclic 3-deoxyachilleol A. The mutated TC of the present invention can convert squalene to monocyclic 3-deoxyachilleol A. Therefore, as shown in FIG. 2, two reactions, i.e. a conversion of squalene to 3-deoxyachilleol A (reaction (a) in FIG. 2), and a conversion of 3-deoxyachilleol A to ambrein (reaction (b) in FIG. 2) can be efficiently carried out by one enzyme.

(Bicyclic Pathway)

In the bicyclic pathway, 8α-hydroxypolypoda-13, 17, 21-triene is produced from squalene by the mutated TC, and then ambrein is produced from 8α-hydroxypolypoda-13, 17, 21-triene by the mutated TC. The conventional wild type TC can convert squalene to 8α-hydroxypolypoda-13, 17, 21-triene, but cannot convert 8α-hydroxypolypoda-13, 17, 21-triene to ambrein. The mutated TC of the present invention can convert 8α-hydroxypolypoda-13, 17, 21-triene to ambrein. Therefore, as shown in FIG. 2, two reactions, i.e. a conversion of squalene to 8α-hydroxypolypoda-13, 17, 21-triene (reaction (c) in FIG. 2), and a conversion of 8α-hydroxypolypoda-13, 17, 21-triene to ambrein (reaction (d) in FIG. 2) can be efficiently carried out by one enzyme.

According to the mutated TC of the present invention, in the process of producing ambrein from squalene, four reactions, i.e. a conversion of squalene to 3-deoxyachilleol A (reaction (a)), a conversion of 3-deoxyachilleol A to ambrein (reaction (b)), a conversion of squalene to 8α-hydroxypolypoda-13, 17, 21-triene (reaction (c)), and a conversion of 8α-hydroxypolypoda-13, 17, 21-triene to ambrein (reaction (d)), can be carried out by one enzyme. The important mutation capable of performing the above four reactions is a mutation in which the 4th aspartic acid of the DXDD motif is substituted with an amino acid other than aspartic acid (for example, D373C). The mutated TC of the first embodiment of the present invention has the substitution of the amino acid adjacent to the N-terminus of a (A/S/G)RX(H/N)XXP motif with the amino acid other than tyrosine (for example, Y167A), or the substitution of the 4th amino acid of the GXGX(G/A/P) motif with the amino acid other than leucine (for example, L596A), in addition to the above substitution, and thus can carry out the reactions of monocyclicpathway and bicyclic pathway by one enzyme.

(Amino Acid Sequence in which One or Plural Amino Acids are Deleted, Substituted, Inserted and/or Added)

A polypeptide of the mutated tetraprenyl-β-curcumene cyclase of the present invention, may be a polypeptide consisting of an amino acid sequence wherein one or plural amino acids are deleted, substituted, inserted and/or added in the amino acid sequence of SEQ ID NO:1. The polypeptide of mutated tetraprenyl-β-curcumene cyclase of the first embodiment exhibits an ambrein production activity using squalene as a substrate, and the polypeptide of mutated tetraprenyl-β-curcumene cyclase of the second embodiment exhibits an ambrein production activity using 3-deoxyachilleol A as a substrate. That is, a polypeptide which does not exhibit an ambrein production activity using squalene as a substrate or 3-deoxyachilleol A respectively, is not comprised in the polypeptide of the mutated tetraprenyl-β-curcumene cyclase of the present invention. The term "amino acid sequence in which one or plural amino acids are deleted, substituted, inserted and/or added" as used herein means an amino acid sequence modified by amino acid substitution or the like. The number of amino acid modifications can be, for example, 1 to 330, 1 to 300, 1 to 250, 1 to 200, 1 to 150, 1 to 100, or 1 to 50, preferably is 1 to 30, more preferably 1 to 10, still more preferably 1 to 5, most preferably 1 to 2. An example of the modified amino acid sequence of the mutated peptide which can be used in the present invention is preferably an amino acid sequence in which the amino acid has one or plural (preferably 1, 2, 3 or 4) conservative substitutions.

(Amino Acid Sequence Having 40% or More Identity with the Amino Acid Sequence)

A polypeptide of the mutated tetraprenyl-β-curcumene cyclase of the present invention, may be a polypeptide consisting of an amino acid sequence having 40% or more identity with the amino acid sequence of SEQ ID NO:1. The polypeptide of mutated tetraprenyl-β-curcumene cyclase of the first embodiment exhibits an ambrein production activity using squalene as a substrate, and the polypeptide of mutated tetraprenyl-β-curcumene cyclase of the second embodiment exhibits an ambrein production activity using 3-deoxyachilleol A as a substrate. That is, a polypeptide which does not exhibit an ambrein production activity using squalene as a substrate or 3-deoxyachilleol A respectively, is not comprised in the polypeptide of the mutated tetraprenyl-β-curcumene cyclase of the present invention. The mutated tetraprenyl-β-curcumene cyclase is a polypeptide consisting of an amino acid sequence preferably having an identity of 45% or more, an amino acid sequence more preferably having an identity of 50% or more, an amino acid sequence more preferably having an identity of 60% or more, an amino acid sequence more preferably having an identity of 70% or more, an amino acid sequence more preferably having an identity of 80% or more, an amino acid sequence more preferably having an identity of 90% or more, an amino acid sequence most preferably having an identity of 95% or more, and having an ambrein production activity from squalene or 3-deoxyachilleol A.

The "amino acid sequence in which one or plural amino acids are deleted, substituted, inserted and/or added" in the amino acid sequence of SEQ ID NO:1 or "amino acid sequence having 40% or more identity with the amino acid sequence" of SEQ ID NO:1 means that the amino acid sequence of SEQ ID NO:1 or 13 is substituted. This substitution in the amino acid sequence is a conservative substitution that maintains the function of the mutated tetraprenyl-β-curcumene cyclase of the present invention. In other words, the term "conservative substitution" means a substitution that does not lose the excellent effects of the mutated tetraprenyl-β-curcumene cyclase of the present invention. That is, even when the insertion, substitution, deletion, or addition is carried out, the ambrein production activity can be improved using squalene or 3-deoxyachilleol A as a substrate. Specifically, the term "conservative substitutions" used herein means that amino acid residue(s) are replaced with different amino acid(s) having similar chemical properties. As for the conservative substitution, there may be mentioned, for example, a substitution of a hydrophobic residue for another hydrophobic residue, or a substitution of a polar residue for another polar residue having the same charge. Functionally similar amino acids that can be used for such substitutions are known in the art for each amino acid. As for nonpolar (hydrophobic) amino acids, there may be mentioned, for example, alanine, valine, isoleucine, leucine, proline, tryptophan, phenylalanine, methionine, or the like. As for polar (neutral) amino acids, there may be mentioned, for example, glycine, serine, threonine, tyrosine, glutamine, asparagine, cysteine, or the like. As for basic amino acids having a positive charge, there may be mentioned, for example, arginine, histidine, lysine, or the like. As for acidic amino acids having a negative charge, there may be mentioned, for example, aspartic acid, glutamic acid, or the like.

In the mutated tetraprenyl-β-curcumene cyclase of the present invention, the mutation (substitution) of the 4th amino acid residue of the DXDD motif, aspartic acid, into the amino acid other than aspartic acid, the mutation (substitution) of the amino acid adjacent to the N-terminus of the (A/S/G)RX(H/N)XXP motif, into the amino acid other than tyrosine, or the mutation (substitution) of the 4th amino acid residue of the GXGX(G/A/P) motif, into the amino acid other than leucine, is an active substitution (mutation) for imparting an activity to produce ambrein using squalene or 3-deoxyachilleol A as a substrate. However, the above conservative substitution is for maintaining the activity to produce ambrein using squalene or 3-deoxyachilleol A as a substrate and can be easily carried out by those skilled in the art.

The mutated tetraprenyl-β-curcumene cyclase of the present invention can be obtained using known genetic recombination techniques and the like. For example, a chromosomal DNA of *Bacillus megaterium* is obtained and tetraprenyl-β-curcumene cyclase is amplified by, for example, PCR using appropriate primers. The obtained gene is inserted into an appropriate vector, and the gene sequence is determined. A gene encoding the mutated tetraprenyl-β-curcumene cyclase of the present invention can be obtained by introducing the above mutation(s). The mutated tetraprenyl-β-curcumene cyclase of the present invention can be obtained by incorporating the resulting gene into a host such as yeast and expressing the same.

Further, the tetraprenyl-β-curcumene cyclase is known to exist in bacteria such as *Bacillus* in addition to *Bacillus megaterium*, and thus it is possible to obtain an enzyme derived from *Bacillus subtilis* (accession number: AB 618206), and an enzyme derived from *Bacillus licheniformis* (accession number: AAU 41134), and the like.

Further, the gene encoding the mutated tetraprenyl-β-curcumene cyclase of the present invention can be synthesized by a known gene synthesis method such as the method of Khorana et al, (Gupta et al., 1968), the method of Narang et al. (Scarpulla et al., 1982) or the method of Rossi et al. (Rossi et al., 1982). Then, the mutated tetraprenyl-β-curcumene cyclase can be obtained by expressing the resulting synthetic gene.

[2] Polynucleotide

The polynucleotide of the present invention is not particularly limited as long as it is a polynucleotide encoding the tetraprenyl-eotide of t cyclase of the present invention. Fax example, there may be mentioned a polynucleotide (SEQ ID NO:7) encoding the polypeptide of SEQ ID NO:5, a polynucleotide (SEQ NO:8) encoding the polypeptide of SEQ ID NO:6, a polynucleotide (SEQ ID NO: 11) encoding the polypeptide of SEQ ID NO:9, a polynucleotide (SEQ ID NO:12) encoding the polypeptide of SEQ ID NO:10, a polynucleotide (SEQ ID NO:14) encoding the polypeptide of SEQ ID NO:13, Further, there may be mentioned a polynucleotide hybridizing under stringent conditions to the polynucleotide consisting of base sequence of SEQ ID NO:7, 8, 11, 12, or 14 and having an ambrein production activity using squalene. In connection to this, the term "polynucleotide" as used herein includes both DNA and RNA.

Further, the polynucleotide of the present invention is preferably changed to base sequence of the optimal codon according to the microorganism or the host cell into which the polynucleotide is introduced.

[3] Microorganism

The microorganism of the present invention has the polynucleotide of the present invention. That is, the microorganism is not particularly limited so long as it includes the polynucleotides of the present invention within cell thereof, and there may be mentioned *Escherichia coli, Bacillus subtilis, Brevibacillus*, Actinomycete, Baker's yeast, *Aspergillus oryzae*, or *Neurospora crassa*.

[4] Vector

The vector of the present invention comprises the DNA having polynucleotide encoding the mutated tetraprenyl-β-curcumene cyclase. That is, the vector of the present invention is not particularly limited, so long as it comprises the polynucleotide of the present invention. As the vector, there may be mentioned, for example, a vector obtained by introducing the polynucleotide of the present invention into a known expression vector appropriately selected in accordance with a host cell to be used.

Preferably, the expression vector is autonomously replicable in the host such as *E. coli*, or baker's yeast, or can be incorporated into the chromosome, and has a high expression efficiency of the foreign protein. The expression vector for expressing the polynucleotide is autonomously replicable in the microorganism, and is preferably a recombinant vector composed of a promoter, a ribosome binding sequence, the DNA and a transcription termination sequence. Further, it may contain a gene controlling the promoter.

More particularly, as an expression vector, for example, pBTrp2, pBTac1, pBTac2 (three vectors are commercially available from Boehringer Mannheim), pKK233-2 (Pharmacia), pSE280 (Invitrogen), pGEMEX-1 (Promega), pQE-8 (QIAGEN), pQE-30 (QIAGEN), pKYP10 (Japanese Unexamined Patent Publication (Kokai) No. 58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescriptII SK+, pBluescriptII SK (−)(Stratagene), pTrS30 (FERMBP-5407), pTrS32 (FERM BP-5408), pGEX (Pharmacia), pET-3 (Novagen), pTerm2 (U.S. Pat. Nos. 4,686,191, 4,939,094, 5,160,735), pSupex, pUB110, pTP5, pC194, pUC18 [gene, 33, 103 (1985)], pUC19 [Gene, 33, 103 (1985)], pSTV28 (TAKARA), pSTV29 (TAKARA), pUC118 (TAKARA), pPA1 (Japanese Unexamined Patent Publication (Kokai) No. 63-233798), pEG400 [J. Bacteriol., 172, 2392 (1990)], pColdI, pColdII, pColdIII, pColdIV, pNIDNA, pNI-HisDNA (TAKARA BIO) and the like can be exemplified.

As the promoter, any one can be used as long as it can be expressed in host cells such as *Escherichia coli*, baker's yeast and the like. For example, there may be mentioned a promoter derived from *Escherichia coli*, phage, or the like, (such as a trp promoter (Ptrp), lac promoter (Plac), PL promoter, PR promoter, or PSE promoter), SPO1 promoter, SPO2 promoter, penP promoter or the like. Further, a promoter designed and modified artificially, such as a promoter (Ptrpx 2) in which two Ptrp are connected in series, tac promoter, let I promoter, or lacT 7 promoter, can also be used. In order to prepare an enzyme for production by an enzymatic method (biosynthesis by in vitro enzymatic reaction using squalene as a substrate), a promoter which functions as a strong promoter and is capable of mass production of a target protein is preferable. In addition; an inducible promoter is more preferable. As the inducible promoter, for example, there may be mentioned a promoter of the cold shock gene cspA which is induced at low temperature, T7 promoter induced by the addition of inducer IPTG, or the like. Further, in a fermentative production (biosynthesis in vivo by a host using a carbon source such as glucose), among the above promoters, a promoter capable of constantly expressing a target gene regardless of tissue, i.e., constitutive promoter is more preferable. As the constitutive promoter, there may mentioned a promoter of an alcohol dehydrogenase 1 gene (ADH1), a translation elongation factor TF-1α gene (TEF1), a phosphoglycerate kinase gene (PGK1), a triose phosphate isomerase gene (TPI1), a triose phosphate dehydrogenase gene (TDH3), or a pyruvate kinase gene (PYK1).

[5] Transformant

The transformant of the present invention is not particularly limited, so long as it comprises the polynucleotide of the present invention. The transformant of the present invention may be, for example, a cell in which the polynucleotide is integrated into a chromosome of a host cell, or a transformant containing the polynucleotide as a vector comprising polynucleotide. Further, the transformant of the present invention may be a transformant expressing the polypeptide of the present invention, or a transformant not expressing the polypeptide of the present invention. The transformant of the present invention may be obtained by, for example, transfecting a desired host cell with the vector of the present invention or the polynucleotide of the present invention per se.

The host cell is not particular limited. A strain which is easy to handle, such as *Escherichia coli, Bacillus subtilis, Brevibacillus*, actinomycete, yeast, *Aspergillus oryzae*, or *Neurospora crassais* is preferable, but insect cells, plant cells, animal cells or the like can be used. However, in order to prepare an enzyme used for production by an enzymatic method (biosynthesis by in vitro enzymatic reaction using squalene as a substrate), *Escherichia coli, Bacillus subtilis, Brevibacillus*, and *Aspergillus oryzae* are preferable, and *Escherichia coli* is most preferable. Further, in a fermentative production (biosynthesis in vivo by a host using a carbon source such as glucose), yeast is most preferable. As the most preferable yeast strain, there may be mentioned sake yeast. The sake yeast Kyokai 7, or Kyokai 701 is more preferable. The strain Kyokai K701 is a non-foaming mutant strain bred from wild-type strain Kyokai K7. However, the strain Kyokai K701's characters other than the above characters are the same as Kyokai K7.

[6] Method for Preparing Ambrein

The first embodiment of the method for preparing ambrein of the present invention is characterized by bringing into contact the mutated tetraprenyl-β-curcumene cyclase with squalene, to obtain ambrein. The second embodiment of the method for preparing ambrein of the present invention is characterized by bringing into contact the mutated tetraprenyl-β-curcumene cyclase with 3-deoxyachilleol A, to obtain ambrein.

The mutated tetraprenyl-β-curcumene cyclase can be prepared by culturing the transformant obtained by introducing the enzyme expression vector into bacteria or the like. The medium used for culturing the transformant may be a commonly used medium and is appropriately selected depending on the type of host. For example, in the case of culturing *E. coli*, LB medium and the like are used. Antibiotics according to the type of selective marker may be added to the medium.

The mutated tetraprenyl-β-curcumene cyclase may be obtained by extraction followed by purification from a culture medium which has been obtained by culturing a transformant capable of expressing the enzyme. Further, it may be expressed as a fusion protein obtained by fusing a trigger factor (TF), a His tag or the like to the N-terminal side or the C-terminal side of the polypeptide of the mutated tetraprenyl-a fusion protein obtained by fusing a trigger factor (TF), a purification and the like may be facilitated. An extraction liquid containing the enzyme, which has been extracted from a transformant in a culture medium, may be used as it is. As a method of extracting an enzyme from a transformant, a known method may be applied. A step of extracting a enzyme may comprise, for example, crushing a transformant in an extraction solvent and separating cell contents from crushed pieces of the transformant. The obtained cell contents contain the mutated tetraprenyl-β-curcumene cyclase of interest.

As the method of crushing a transformant, a known method in which a transformant is crushed and an enzyme liquid can be recovered may be applied, and examples thereof include ultrasonic crushing and glass beads crushing. The conditions of crushing are not particularly restricted as long as the enzyme is not inactivated, such as a condition of not higher than 10° C. and for 15 minutes.

Examples of the method of separating cell contents from crushed pieces of microorganism include sedimentation, centrifugation, filtering separation, and a combination of two or more thereof. Conditions for these separation methods are known to those skilled in the art. The conditions are, for example, from 8,000×g to 15,000×g and from 10 to 20 minutes in the case of centrifugation.

The extraction solvent may be a solvent which is usually used as a solvent for extracting an enzyme, and examples thereof include Tris-HCl buffer and potassium phosphate buffer. The pH of an extraction solvent is, from the viewpoint of enzyme stability, preferably from 3 to 10 and more preferably from 6 to 8.

The extraction solvent may contain a surfactant. Examples of the surfactant include a nonionic surfactant and an ampholytic surfactant. Examples of the nonionic surfactant include: a polyoxyethylene sorbitan fatty acid ester such as poly(oxyethylene)sorbitan monooleate (Tween 80); alkylglucoside such asn-octylβ-D-glucoside; a sucrose fatty acid ester such as sucrose stearate; and a polyglycerol fatty acid ester such as polyglycerol stearate. Examples of the ampholytic surfactant include N,N-dimethyl-N-dodecylglycine betaine which is an alkylbetaine. Besides the above, surfactants generally used in the art such as Triton X-100 (TRITON X-100), polyoxyethylene(20)cetyl ether (BRIJ-58), and nonylphenol ethoxylate (TERGITOL NP-40) can be utilized.

The concentration of a surfactant in an extraction solvent is, from the viewpoint of enzyme stability, preferably from 0.001% by mass to 10% by mass, more preferably from 0.10% by mass to 3.0% by mass, and further preferably from 0.10% by mass to 1.0% by mass.

From the viewpoint of enzyme activity, an extraction solvent preferably contains a reducing agent such as dithiothreitol or β-mercaptoethanol. The reducing agent is preferably dithiothreitol. The concentration of dithiothreitol in an extraction solvent is preferably from 0.1 mM to 1M and more preferably from 1 mM to 10 mM. In a case that dithiothreitol is present in an extraction solvent, a structure such as a disulfide bond in the enzyme is easily to be retained and enzyme activity is easily to be enhanced.

From the viewpoint of enzyme activity, the extraction solvent preferably contains chelating agent such as ethylenediaminetetraacetic acid (EDTA). The concentration of EDTA in the extraction solvent is preferably from 0.01 mM to 1 M and more preferably from 0.1 mM to 10 mM. In a case that EDTA is present in the extraction solvent, a metal ion which may reduce enzyme activity is chelated, and therefore, enzyme activity is easily to be enhanced.

The extraction solvent may contain, besides the ingredients described above, a known ingredient which can be added to an enzyme extraction solvent.

The mutated tetraprenyl-β-curcumene cyclase may be used singly, or in combination of two or more kinds thereof.

The conditions of a reaction between the mutated tetraprenyl-β-curcumene cyclase and squalene or 3-deoxyachilleol A are not particularly restricted as long as the conditions are such that an enzyme reaction can be proceeded. For example, the reaction temperature and the reaction time may be appropriately selected based on the activity of the mutated tetraprenyl-β-curcumene cyclase or the like. From the viewpoint of reaction efficiency, the reaction temperature and the reaction time may be, for example, from 4° C. to 100° C. and from 1 hour to 30 days, and preferably 30° C. to 60° C. and 16 hours to 20 days. From the viewpoint of reaction efficiency, the pH is, for example, from 3 to 10, and preferably from 6 to 8.

A reaction solvent is not particularly restricted as long as the reaction solvent does not inhibit an enzyme reaction, and a buffer or the like which is usually used can be used. For example, the same solvent as an extraction solvent which is used in a step of extracting an enzyme can be used. An extraction liquid (for example, cell-free extract) containing the mutated tetraprenyl-β-curcumene cyclase may be used as it is as an enzyme liquid in the reaction.

From the viewpoint of reaction efficiency, the concentration ratio between mutated tetraprenyl-β-curcumene cyclase and squalene or 3-deoxyachilleol A which is the substrate thereof in a production reaction of ambrein is preferably from 1 to 10000, more preferably from 10 to 5000, still more preferably from 100 to 3000, and still further preferably from 1000 to 2000 in terms of the molar concentration ratio (substrate/enzyme) of the substrate to the enzyme.

From the viewpoint of reaction efficiency, the concentration of squalene or 3-deoxyachilleol A to be used for an enzyme reaction is preferably from 0.000001% by mass to 10% by mass, and more preferably from 0.00001% by mass to 1% by mass with respect to the total mass of the reaction solvent.

The reaction step between the mutated tetraprenyl-β-curcumene cyclase and squalene or 3-deoxyachilleol A may be repeated a plurality of times. This can increase the yield of ambrein. In the case that a plurality of reaction steps are repeated, the purification method may be comprised: a step of recharging squalene or 3-deoxyachilleol A to be the substrate; a step of recovering and purifying a reaction product in a reaction liquid after inactivating the enzyme by a known method; and the like. In a case that squalene is recharged, a charging point in time, and the amount of charging of squalene can be appropriately set according to the concentration of the mutated tetraprenyl-β-curcumene cyclase in the reaction liquid, the amount of the substrate remained in the reaction liquid, or the like.

According to another embodiment of the preparation method of the present invention, it is characterized by culturing the microorganism or the transformant of the present invention.

An ambrein can be prepared by culturing the microorganism or the host cell transformed with the expression vector. Regarding the yeast, the yeast may be cultured in a conventional YPD medium and the like. For example, the yeast wherein a gene is introduced by a homologous recombination, or the yeast having the expression vector, is precultured. Then, the precultured yeast is inoculated to an YPD medium or the like, and it is cultured for about 24 to 240 hours, preferably about 72 to 120 hours. The ambrein which is secreted into the medium can be used as is, or after a purification by the known method. In particular, as the purification method, there may be mentioned solvent extraction, recrystallization, distillation, column chromatography, and HPLC.

EXAMPLES

The present invention now will be further illustrated by, but is by no means limited to, the following Examples.

*Bacillus megaterium* is sometimes abbreviated as "Bme" in the specification, figures, or Tables, and tetraprenyl-β-curcumene cyclase derived from *Bacillus megaterium* is sometimes abbreviated as "BmeTC.

Example 1

In this Example, the mutated tetraprenyl-β-curcumene cyclase was cloned and an expression vector was constructed.

A polynucleotide encoding wild type tetraprenyl-β-curcumene cyclase was obtained by PCR using *Bacillus megaterium* chromosomal DNA as a template, and an amino acid sequence of the wild type enzyme was determined. (Hereinafter, unless otherwise noted, tetraprenyl-β-curcumene cyclase has a sequence derived from *Bacillus megaterium*, and is sometimes simply referred to as "wild type.")

The mutated tetraprenyl-β-curcumene cyclase gene was designed based on the amino acid sequence of the wild type enzyme, so that aspartic acid at position 373 is substituted with cysteine, and tyrosine at position 167 is substituted with alanine, and was synthesized by optimizing codons for *Escherichia coli* of the host. The synthesized gene was inserted into the cloning site (restriction enzyme EcoRV site) of the vector pColdTF (TAKARA BIO), to obtain the expression vector containing the mutated tetraprenyl-β-curcumene cyclase gene of Y167A/D373C mutant (SEQ ID NO:5).

Then, a transformant of *Escherichia coli* BL21 (DE3) was prepared using the obtained expression vector containing the mutated tetraprenyl-β-curcumene cyclase gene.

Example 2

In this Example, the mutated tetraprenyl-β-curcumene cyclase gene wherein aspartic acid at position 373 is substituted with cysteine, and leucine at position 596 is substituted with alanine, was constructed.

The mutated tetraprenyl-β-curcumene cyclase gene was designed based on the amino acid sequence of the wild type enzyme, so that aspartic acid at position 373 is substituted with cysteine, and leucine at position 596 is substituted with alanine, and was synthesized by optimizing codons for *Escherichia coli* of the host. The synthesized gene was inserted into the cloning site (restriction enzyme EcoRV site) of the vector pColdTF (TAKARA BIO), to obtain the expression vector containing the mutated tetraprenyl-β-curcumene cyclase gene of D373C/L596A mutant (SEQ ID NO:6).

Then, a transformant of *Escherichia coli* BL21 (DE3) was prepared using the obtained expression vector containing the mutated tetraprenyl-β-curcumene cyclase gene.

Comparative Examples 1 to 3

In this Comparative Example, expression vectors of the mutated tetraprenyl-β-curcumene cyclases wherein only one amino acid at position 373, 167, and 596 was substituted, were constructed.

The procedure described in Example 1 was repeated except that a site-specific mutation was introduced thereinto by a Quick Change method so that aspartic acid at position 373 was substituted with cysteine, a site-specific mutation was introduced thereinto by a Quick Change method so that tyrosine at position 167 was substituted with alanine, or a site-specific mutation was introduced thereinto by a Quick Change method so that leucine at position 596 was substituted with alanine, to obtain the expression vectors and transformants of D373C mutant (Comparative Example 1), Y167A mutant (Comparative Example 2) or L596A mutant (Comparative Example 3).

Codons optimized for *E. coli* of host were used.

Example 3 and Comparative Example 4

In this Example and Comparative Example, enzyme activities of the mutated tetraprenyl-β-curcumene cyclases were examined using squalene as a substrate.

The transformants prepared in Example 1, Example2, and Comparative Examples 1 to 3 were respectively inoculated in the LB medium (1 L) containing ampicillin (50 mg/L) and the whole were cultivated at 37° C., for 3 hours while shaking. After cultivation, isopropyl-β-thiogalactopyranoside (IPTG:0.1M) was added thereto, the whole was shaken at 15° C., for 24 hours, to induce the expression of the mutated tetraprenyl-β-curcumene cyclases.

Thereafter, the bacterial cells collected by centrifugation (6,000×g, 10 minutes) were washed with 50 mM Tris-HCl buffer (pH 7.5). Then, the bacterial cells (5 g) were suspended in 15 mL of buffer A [containing 50 mM Tris-HCl buffer (pH 7.5), 0.1 v/v % Tween80, 0.1 v/v % sodium ascorbate, 2.5 mM dithiothreitol, 1 mM EDTA], and the suspension was sonicated at 4° C., for 20 minutes, using UP2005 sonicator (Hielscher Ultrasonics, Teltow, Germany). The sonicated sample was centrifuged at 12,300×g, for 20 minutes, and the supernatant obtained after centrifugation was used as a cell-free extract solutions A to E. (Hereinafter, the cell-free extracts prepared by using the transformants in Example 1 and 2 were designated as cell-free extracts A and B, respectively, and the cell-free extracts prepared by using the transformants in Comparative Examples 1 to 3 were designated as cell-free extracts C to E, respectively.)

Squalene (100 μg) was mixed with Triton Tween80 (5 mg) for solubilization and then added to buffer A (1 mL) to prepare a squalene solution. The whole amount of the squalene solution was added to cell-free extract A (4 mL) to prepare a reaction solution and incubated at 30° C., for 64 hours. The molar ratio (substrate/enzyme) of squalene (substrate) to the mutated tetraprenyl-β-curcumene cyclase (enzyme) in the reaction solution was about 200.

After the incubation, 15% potassium hydroxide in methanol (6 mL) was added to the reaction solution to stop the enzymatic reaction. Then, n-hexane (5 mL) was added to the reaction solution, and the reaction product was extracted three times.

Figure 3:
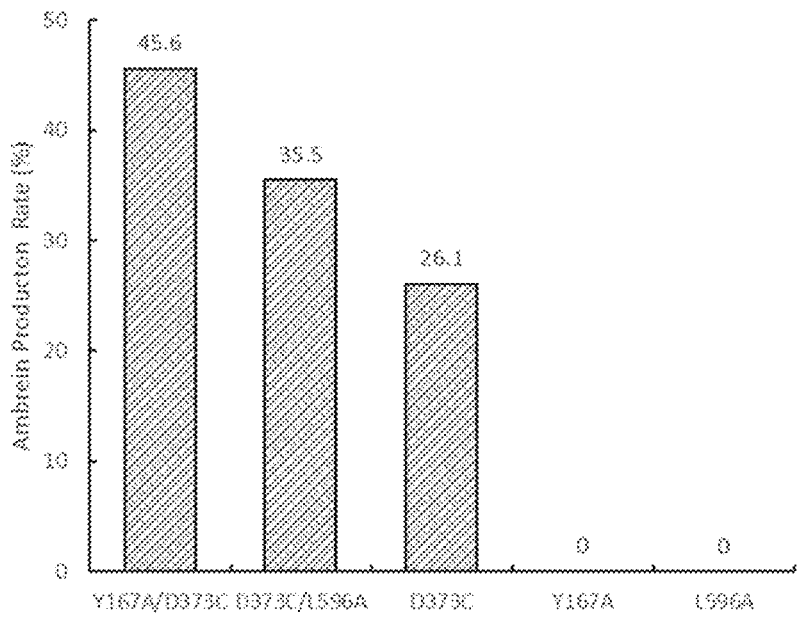
FIG. 3 is a graph showing a production efficiency of ambrein using squalene as a substrate by using Y167A/D373C mutant (Example 1), D373C/L596A mutant (Example 2), D373C mutant (Comparative Example 1), Y167A mutant (Comparative Example 2), and L596A mutant (Comparative Example 3).

Ambrein production rates of the resulting extracts are shown in FIG. 3. The amounts of ambrain production of the Y167A/D373C mutant obtained in Example 1 and the D373C/L596A mutant obtained in Example 2 were improved, compared with the D373 mutant. On the other hand, the Y167A mutant obtained in Comparative Example 2 and the L596A mutant obtained in Comparative Example 3 cannot produce ambrain.

Figure 4:
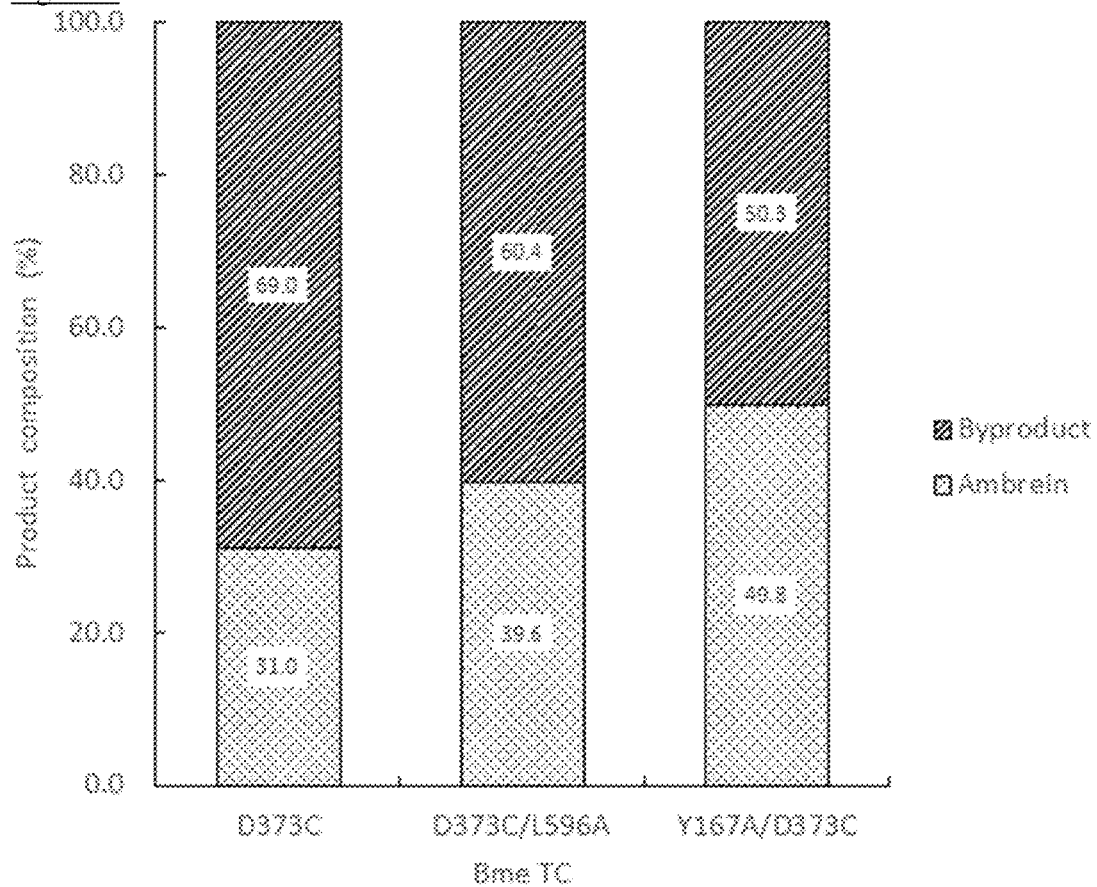
FIG. 4 is a graph showing the rate of ambrein and the other reaction products (by-products) in the enzymatic reaction using squalene as a substrate by using Y167A/D373C mutant (Example 1), D373C/L596A mutant (Example 2), and D373C mutant (Comparative Example 1).

In addition, the production rate of ambrain and by-products is shown in FIG. 4. The reaction selectivity from squalene (substrate) to ambrain is improved, and thus the Y167A/D373C mutant and the D373C/L596A mutant can produce ambrein efficiently. In addition, the identification of the ambrein and the calculation of the production rate were performed by GC/MS and NMR The identification of ambrein and the calculation of the production rate were performed by GC/MS and NMR.

Example 4

Figure 5:
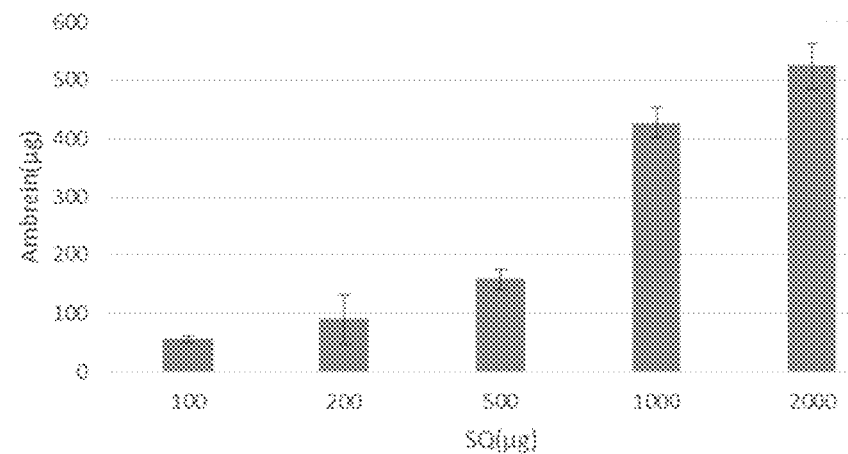
FIG. 5 is a graph showing the productivity of ambrein using squalene as a substrate by using Y167A/D373C mutant (Example 1), and changing the substrate concentration.

In this Example, the productivity of ambrein of the mutated tetraprenyl-β-curcumene cyclase was examined using squalene as a substrate by using Y167A/D373C mutant obtained in Example 1, and changing the substrate concentration. The procedure described in Example 3 was repeated except that the substrate concentration was changed. The results are shown in FIG. 5. 427 μg of ambrein could be produced from 1000 μg of squalene, and the reaction efficiency was 43%.

Example 5

In this Example, the mutated tetraprenyl-β-curcumene cyclase was cloned and an expression vector was constructed. The mutated tetraprenyl-β-curcumene cyclase gene was designed based on the amino acid sequence of the wild type enzyme, so that leucine at position 596 is substituted with alanine, and was synthesized by optimizing codons for *Escherichia coli* of the host. The synthesized gene was inserted into the cloning site (restriction enzyme EcoRV site) of the vector pColdTF (TAKARA BIO), to obtain the expression vector containing the mutated tetraprenyl-β-curcumene cyclase gene of L596A mutant (SEQ ID NO:9).

Then, a transformant of *Escherichia coli* BL21 (DE3) was prepared using the obtained expression vector containing the mutated tetraprenyl-β-curcumene cyclase gene.

(Transformant Producing L596A Mutant Enzyme)

Example 6

In this Example, the mutated tetraprenyl-β-curcumene cyclase gene wherein leucine at position 596 is substituted with alanine, was constructed.

The procedure described in Example 5 was repeated except that a site-specific mutation was introduced thereinto so that leucine at position 596 was substituted with alanine, to obtain the expression vector containing the mutated tetraprenyl-β-curcumene cyclase gene (codons were optimized for *Escherichia coli* of the host) of L596F mutant (SEQ ID NO:10). Then, a transformant of *Escherichia coli* BL21 (DE3) was prepared using the obtained expression vector containing the mutated tetraprenyl-β-curcumene cyclase gene. (Transformant producing L596F mutant enzyme)

Comparative Example 5

In this Comparative Example, the wild type tetraprenyl-β-curcumene cyclase was cloned and an expression vector was constructed.

The procedure described in Example 5 was repeated except that a site-specific mutation for substituting leucine at position 596 with alanine was not introduced thereinto, to obtain the expression vector containing the tetraprenyl-β-curcumene cyclase gene having leucine at position 596 (codons were optimized for *Escherichia coli* of the host). Then, a transformant of *Escherichia coli* BL21 (DE3) was prepared using the obtained expression vector containing the mutated tetraprenyl-β-curcumene cyclase gene.

(Transformant Producing Wild Type Enzyme)

Example 7

In this Example, the mutated tetraprenyl-β-curcumene cyclase gene wherein leucine at position 596 is substituted with valine, was constructed.

The procedure described in Example 5 was repeated except that a site-specific mutation was introduced thereinto so that leucine at position 596 was substituted with valine, to obtain the expression vector containing the mutated tetraprenyl-β-curcumene cyclase gene of L596V mutant (codons were optimized for Escherichia coli of the host). Then, a transformant of Escherichia coli BL21 (DE3) was prepared using the obtained expression vector containing the mutated tetraprenyl-β-curcumene cyclase gene.
(Transformant Producing L596V Mutant Enzyme)

Comparative Example 6

In this Comparative Example, the mutated tetraprenyl-β-curcumene cyclase gene wherein leucine at position 596 is substituted with proline, was constructed.

The procedure described in Example 5 was repeated except that a site-specific mutation was introduced thereinto so that leucine at position 596 was substituted with proline, to obtain the expression vector containing the mutated tetraprenyl-β-curcumene cyclase gene of L596P mutant (codons were optimized for Escherichia coli of the host). Then, a transformant of Escherichia coli BL21 (DE3) was prepared using the obtained expression vector containing the mutated tetraprenyl-β-curcumene cyclase gene.
(Transformant Producing L596P Mutant Enzyme)

Example 8 and Comparative Example 7

In this Example and Comparative Example, enzyme activities of the mutated tetraprenyl-β-curcumene cyclases were examined using 3-deoxyachilleol A as a substrate.

The transformants prepared in Examples 5 to 7, and Comparative Examples 1 to 3 were respectively inoculated in the LB medium (1 L) containing ampicillin (50 mg/L) and the whole were cultivated at 37° C., for 3 hours while shaking. After cultivation, isopropyl-β-thiogalactopyranoside (IPTG:0.1M) was added thereto, the whole was shaken at 15° C., for 24 hours, to induce the expression of the mutated tetraprenyl-β-curcumene cyclases.

Thereafter, the bacterial cells collected by centrifugation (6,000×g, 10 minutes) were washed with 50 mM Tris-HCl buffer (pH 7.5). Then, the bacterial cells (5 g) were suspended in 15 mL of buffer A [containing 50 mM Tris-HCl buffer (pH 7.5), 0.1 v/v % Tween80, 0.1 v/v % sodium ascorbate, 2.5 mM dithiothreitol, 1 mM EDTA], and the suspension was sonicated at 4° C., for 20 minutes, using UP2005 sonicator (Hielscher Ultrasonics, Teltow, Germany). The sonicated sample was centrifuged at 12,300×g, for 20 minutes, and the supernatant obtained after centrifugation was used as a cell-free extract solutions F to J. (Hereinafter, the cell-free extracts prepared by using the transformants in Example 5 to 7 were designated as cell-free extracts F to H, respectively, and the cell-free extracts prepared by using the transformants in Comparative Examples 5 to 6 were designated as cell-free extracts I to J, respectively.)

3-deoxyachilleol A (100 μg) was mixed with Triton Tween80 (2 mg) for solubilization and then added to buffer A (1 mL) to prepare a 3-deoxyachilleol A solution. The whole amount of the 3-deoxyachilleol A solution was added to each of cell-free extracts F to J (4 mL) to prepare a reaction solution and incubated at 30° C., for 112 hours. The molar ratio (substrate/enzyme) of 3-deoxyachilleol A (substrate) to the mutated tetraprenyl-β-curcumene cyclase (enzyme) in the reaction solution was about 200.

After the incubation, 15% potassium hydroxide in methanol (6 mL) was added to the reaction solution to stop the enzymatic reaction. Then, n-hexane (5 mL) was added to the reaction solution, and the reaction product was extracted three times.

Figure 6:
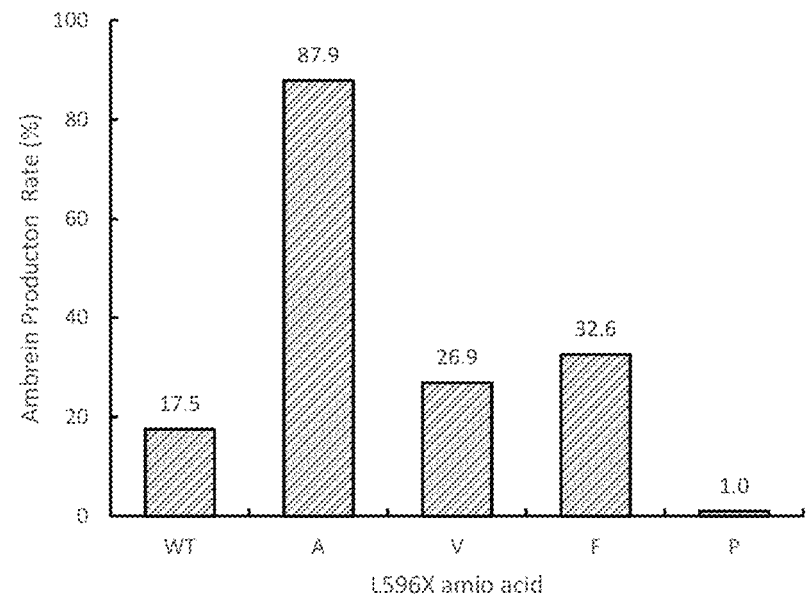
FIG. 6 is a graph showing a production efficiency using 3-deoxyachilleol A as a substrate by using L596A mutant (Example 5), L596F mutant (Example 6), wild type (Comparative Example 5), L596V mutant (Example 7), L596P mutant (Comparative Example 6).

Ambrein production rates of the resulting extracts are shown in FIG. 6. As a result, in the L596A mutant, L596F mutant, and L596V mutant, ambrein was obtained with high conversion efficiency. In particular, in the L596Avarian had few by-product, and 94% of the product was ambrein. On the other hand, the wild-type tetraprenyl-β-curcumene cyclase produced little ambrain and had a high by-products ratio.

In addition, the production rate of ambrain and by-products is shown in FIG. 7. 4. The reaction selectivity from 3-deoxyachilleol A (substrate) to ambrain is improved, and thus the L596A mutant can produce ambrein efficiently.

INDUSTRIAL APPLICABILITY

According to the present invention, in the production of ambrein, it is possible to produce ambrein in one step using squalene as a substrate by using the mutated tetraprenyl-β-curcumene cyclase. Ambrein obtained by the present invention can be used, for example, as a raw material for production of pharmaceuticals and the like.

---

The invention claimed is:

1. A mutated tetraprenyl-β-curcumene cyclase wherein
(1-1) a 4th amino acid residue of a DXDD motif, aspartic acid, is substituted with cysteine, and
(2-1) an amino acid adjacent to the N-terminus of an (A/S/G)RX(H/N)XXP motif is substituted with alanine, or a 4th amino acid of the GXGX(G/A/P) motif is substituted with alanine, (a) having 90% or more sequence identity with the amino acid sequence of SEQ ID NO: 1, and (b) exhibiting ambrein production activity using squalene as a substrate; or (1-2) the mutated tetraprenyl-β-curcumene cyclase has the DXDD motif, and
(2-2) a 4th amino acid of the GXGX(G/A/P) motif is alanine, phenylalanine, or valine, having (a) having 90% or more sequence identity with the amino acid sequence of SEQ ID NO: 1, and (b) exhibiting ambrein production activity using 3-deoxyachilleol A as a substrate.

2. The mutated tetraprenyl-β-curcumene cyclase according to claim 1, wherein a polypeptide constituting the mutated tetraprenyl-β-curcumene cyclase is (1) a polypeptide wherein aspartic acid at position 373 from the N-terminal in the amino acid sequence of SEQ ID NO: 1 is substituted with cysteine; and tyrosine at position 167 from the N-terminal in the amino acid sequence of SEQ ID NO: 1 is substituted with alanine, or leucine at position 596 from the N-terminal in the amino acid sequence of SEQ ID NO: 1 is substituted with alanine,
(2) a polypeptide wherein one or plural amino acids are deleted, substituted, inserted and/or added in the amino acid sequence in which aspartic acid at position 373 from the N-terminal in the amino acid sequence of SEQ ID NO: 1 is substituted with cysteine; and tyrosine at position 167 from the N-terminal in the amino acid sequence of SEQ ID NO: 1 is substituted with alanine, or leucine at position 596 from the N-terminal in the amino acid sequence of SEQ ID NO: 1 is substituted with alanine, and exhibiting ambrein production activity using squalene as a substrate,
(3) a polypeptide having 90% or more sequence identity with the amino acid sequence in which aspartic acid at position 373 from the N-terminal in the amino acid sequence of SEQ ID NO: 1 is substituted with cysteine; and tyrosine at position 167 from the N-terminal in the amino acid sequence of SEQ ID NO: 1 is substituted with alanine, or leucine at position 596 from the N-terminal in the amino acid sequence of SEQ ID NO: 1 is substituted with an amino acid other than leucine, and exhibiting ambrein production activity using squalene as a substrate,
(4) a polypeptide comprising the amino acid sequence in which aspartic acid at position 373 from the N-terminal in the amino acid sequence of SEQ ID NO: 1 is substituted with cysteine; and tyrosine at position 167 from the N-terminal in the amino acid sequence of SEQ ID NO: 1 is substituted with alanine, or leucine at position 596 from the N-terminal in the amino acid sequence of SEQ ID NO: 1 is substituted with alanine, and exhibiting ambrein production activity using squalene as a substrate,
(5) a polypeptide comprising the amino acid sequence wherein one or plural amino acids are deleted, substituted, inserted and/or added in the amino acid sequence in which aspartic acid at position 373 from the N-terminal in the amino acid sequence of SEQ ID NO: 1 is substituted with cysteine; and tyrosine at position 167 from the N-terminal in the amino acid sequence of SEQ ID NO: 1 is substituted with alanine, or leucine at position 596 from the N-terminal in the amino acid sequence of SEQ ID NO: 1 is substituted with alanine, and exhibiting ambrein production activity using squalene as a substrate, or
(6) a polypeptide comprising an amino acid sequence having 90% or more sequence identity with the amino acids sequence in which aspartic acid at position 373 from the N-terminal in the amino acid sequence of SEQ ID NO: 1 is substituted with cysteine; and tyrosine at position 167 from the N-terminal in the amino acid sequence of SEQ ID NO: 1 is substituted with alanine, or leucine at position 596 from the N-terminal in the amino acid sequence of SEQ ID NO: 1 is substituted with alanine, and exhibiting ambrein production activity using squalene as a substrate.

3. A polynucleotide encoding the mutated tetraprenyl-β-curcumene cyclase according to claim 1.
4. A microorganism having the polynucleotide according to claim 3.
5. A vector comprising a DNA having the polynucleotide according to claim 3.
6. A transformant having the vector according to claim 5.
7. A method for preparing ambrein characterized by bringing into contact the mutated tetraprenyl-β-curcumene cyclase according to claim 1 with squalene, to obtain ambrein.
8. A method for preparing ambrein characterized by bringing into contact the mutated tetraprenyl-β-curcumene cyclase according claim 1 with 3-deoxyachilleol A, to obtain ambrein.
9. A method for preparing ambrein characterized by culturing the microorganism according claim 4.
10. A method for preparing ambrein characterized by bringing into contact the mutated tetraprenyl-β-curcumene cyclase according to claim 1 or 2 with 8α-hydroxypolypoda-13, 17, 21-triene, to obtain ambrein.
11. The mutated tetraprenyl-β-curcumene cyclase according to claim 1, wherein a polypeptide constituting the mutated tetraprenyl-β-curcumene cyclase is
(1) a polypeptide wherein leucine at position 596 from the N-terminal in the amino acid sequence of SEQ ID NO: 1 is substituted with alanine, phenylalanine, or valine,
(2) a polypeptide wherein one or plural amino acids are deleted, substituted, inserted and/or added in the amino acid sequence in which leucine at position 596 from the N-terminal in the amino acid sequence of SEQ ID NO: 1 is substituted with alanine, phenylalanine, or valine, and exhibiting ambrein production activity using 3-deoxyachilleol A as a substrate,
(3) a polypeptide having 90% or more sequence identity with the amino acid sequence in which leucine at position 596 from the N-terminal in the amino acid sequence of SEQ ID NO: 1 is substituted with alanine, phenylalanine, or valine, and exhibiting ambrein production activity using 3-deoxyachilleol A as a substrate,
(4) a polypeptide comprising the amino acid sequence in which leucine at position 596 from the N-terminal in the amino acid sequence of SEQ ID NO: 1 is substituted with alanine, phenylalanine, or valine, and exhibiting ambrein production activity using 3-deoxyachilleol A as a substrate,
(5) a polypeptide comprising the amino acid sequence wherein one or plural amino acids are deleted, substituted, inserted and/or added in the amino acid sequence in which leucine at position 596 from the N-terminal in the amino acid sequence of SEQ ID NO: 1 is substituted with alanine, phenylalanine, or valine, and exhibiting ambrein production activity using 3-deoxyachilleol A as a substrate, or
(6) a polypeptide comprising an amino acid sequence having 90% or more sequence identity with the amino acid sequence in which leucine at position 596 from the N-terminal in the amino acid sequence of SEQ ID NO: 1 is substituted with alanine, phenylalanine, or valine, and exhibiting ambrein production activity using 3-deoxyachilleol A as a substrate.

\* \* \* \* \*

SEQUENCE LISTING

```
<160> NUMBER OF SEQ ID NOS: 14

<210> SEQ ID NO 1
<211> LENGTH: 625
<212> TYPE: PRT
<213> ORGANISM: Bacillus megaterium

<400> SEQUENCE: 1

Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
```

```
                    35                  40                  45
Thr Phe Asp Leu Asp Lys Glu Val Leu Ile Lys Gln Leu Thr Glu Arg
 50                  55                  60
Ile Val Ser Leu Gln Asn Glu Asp Gly Leu Trp Thr Leu Phe Asp Asp
 65                  70                  75                  80
Glu Glu His Asn Leu Ser Ala Thr Ile Gln Ala Tyr Thr Ala Leu Leu
                 85                  90                  95
Tyr Ser Gly Tyr Tyr Gln Lys Asn Asp Arg Ile Leu Arg Lys Ala Glu
                100                 105                 110
Arg Tyr Ile Ile Asp Ser Gly Gly Ile Ser Arg Ala His Phe Leu Thr
            115                 120                 125
Arg Trp Met Leu Ser Val Asn Gly Leu Tyr Glu Trp Pro Lys Leu Phe
            130                 135                 140
Tyr Leu Pro Leu Ser Leu Leu Val Pro Thr Tyr Val Pro Leu Asn
145                 150                 155                 160
Phe Tyr Glu Leu Ser Thr Tyr Ala Arg Ile His Phe Val Pro Met Met
                165                 170                 175
Val Ala Gly Asn Lys Lys Phe Ser Leu Thr Ser Arg His Thr Pro Ser
            180                 185                 190
Leu Ser His Leu Asp Val Arg Glu Gln Lys Gln Ser Glu Glu Thr
        195                 200                 205
Thr Gln Glu Ser Arg Ala Ser Ile Phe Leu Val Asp His Leu Lys Gln
210                 215                 220
Leu Ala Ser Leu Pro Ser Tyr Ile His Lys Leu Gly Tyr Gln Ala Ala
225                 230                 235                 240
Glu Arg Tyr Met Leu Glu Arg Ile Glu Lys Asp Gly Thr Leu Tyr Ser
                245                 250                 255
Tyr Ala Thr Ser Thr Phe Phe Met Ile Tyr Gly Leu Leu Ala Leu Gly
                260                 265                 270
Tyr Lys Lys Asp Ser Phe Val Ile Gln Lys Ala Ile Asp Gly Ile Cys
            275                 280                 285
Ser Leu Leu Ser Thr Cys Ser Gly His Val His Val Glu Asn Ser Thr
        290                 295                 300
Ser Thr Val Trp Asp Thr Ala Leu Leu Ser Tyr Ala Leu Gln Glu Ala
305                 310                 315                 320
Gly Val Pro Gln Gln Asp Pro Met Ile Lys Gly Thr Thr Arg Tyr Leu
                325                 330                 335
Lys Lys Arg Gln His Thr Lys Leu Gly Asp Trp Gln Phe His Asn Pro
            340                 345                 350
Asn Thr Ala Pro Gly Gly Trp Gly Phe Ser Asp Ile Asn Thr Asn Asn
        355                 360                 365
Pro Asp Leu Asp Thr Ser Ala Ala Ile Arg Ala Leu Ser Arg Arg
370                 375                 380
Ala Gln Thr Asp Thr Asp Tyr Leu Glu Ser Trp Gln Arg Gly Ile Asn
385                 390                 395                 400
Trp Leu Leu Ser Met Gln Asn Lys Asp Gly Gly Phe Ala Ala Phe Glu
                405                 410                 415
Lys Asn Thr Asp Ser Ile Leu Phe Thr Tyr Leu Pro Leu Glu Asn Ala
            420                 425                 430
Lys Asp Ala Ala Thr Asp Pro Ala Thr Ala Asp Leu Thr Gly Arg Val
        435                 440                 445
Leu Glu Cys Leu Gly Asn Phe Ala Gly Met Asn Lys Ser His Pro Ser
450                 455                 460
```

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
            485                 490                 495

Ala Ile Thr Gly Leu Arg Ala Val Gly Val Ser Ala Ser Asp Pro Arg
            500                 505                 510

Ile Ile Lys Ala Ile Asn Trp Leu Lys Ser Ile Gln Gln Glu Asp Gly
            515                 520                 525

Gly Phe Gly Glu Ser Cys Tyr Ser Ala Ser Leu Lys Lys Tyr Val Pro
            530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
            565                 570                 575

Phe Leu Leu Asn Pro Asn Leu Thr Glu Gln Gln Thr His Tyr Pro Thr
            580                 585                 590

Gly Ile Gly Leu Pro Gly Gln Phe Tyr Ile Gln Tyr His Ser Tyr Asn
            595                 600                 605

Asp Ile Phe Pro Leu Leu Ala Leu Ala His Tyr Ala Lys Lys His Ser
610                 615                 620

Ser
625

<210> SEQ ID NO 2
<211> LENGTH: 632
<212> TYPE: PRT
<213> ORGANISM: Bacillus subtilis

<400> SEQUENCE: 2

Met Gly Thr Leu Gln Glu Lys Val Arg Arg Tyr Gln Lys Lys Thr Ile
1               5                   10                  15

Ala Glu Leu Lys Asn Arg Gln Asn Ala Asp Gly Ser Trp Thr Phe Cys
            20                  25                  30

Phe Glu Gly Pro Ile Met Thr Asn Ser Phe Phe Ile Leu Leu Leu Thr
        35                  40                  45

Ser Leu Asp Glu Gly Glu Asn Glu Lys Glu Leu Ile Ser Ala Leu Ala
50                  55                  60

Ala Gly Ile Arg Glu Lys Gln Gln Pro Asp Gly Thr Phe Ile Asn Tyr
65                  70                  75                  80

Pro Asp Glu Thr Ser Gly Asn Ile Thr Ala Thr Val Gln Gly Tyr Val
            85                  90                  95

Gly Met Leu Ala Ser Gly Cys Phe His Arg Ser Asp Pro His Met Arg
            100                 105                 110

Lys Ala Glu Gln Ser Ile Ile Ser His Gly Gly Leu Arg His Val His
            115                 120                 125

Phe Met Thr Lys Trp Met Leu Ala Val Asn Gly Leu Tyr Pro Trp Pro
            130                 135                 140

Val Leu Tyr Leu Pro Leu Ser Leu Met Ala Leu Pro Pro Thr Leu Pro
145                 150                 155                 160

Val His Phe Tyr Gln Phe Ser Ala Tyr Ala Arg Ile His Phe Ala Pro
            165                 170                 175

Met Ala Val Thr Leu Asn Gln Arg Phe Val Leu Lys Asn Arg Asn Ile
            180                 185                 190

Pro Ser Leu Arg His Leu Asp Pro His Met Thr Lys Asn Pro Phe Thr

-continued

```
            195                 200                 205
Trp Leu Arg Ser Asp Ala Phe Glu Glu Arg Asp Leu Thr Ser Ile Trp
210                 215                 220

Ser His Trp Asn Arg Ile Phe His Ala Pro Phe Ala Phe Gln Gln Leu
225                 230                 235                 240

Gly Leu Gln Thr Ala Lys Thr Tyr Met Leu Asp Arg Ile Glu Lys Asp
                245                 250                 255

Gly Thr Leu Tyr Ser Tyr Ala Ser Ala Thr Ile Phe Met Val Tyr Ser
                260                 265                 270

Leu Leu Ser Leu Gly Val Ser Arg Tyr Ser Pro Val Ile Lys Arg Ala
                275                 280                 285

Ile Asn Gly Ile Lys Ser Leu Met Thr Lys Cys Asn Gly Ile Pro Tyr
290                 295                 300

Leu Glu Asn Ser Thr Ser Thr Val Trp Asp Thr Ala Leu Ile Ser Tyr
305                 310                 315                 320

Ala Leu Gln Lys Asn Gly Val Thr Glu Thr Asp Gly Ser Ile Thr Lys
                325                 330                 335

Ala Ala Ala Tyr Leu Leu Glu Arg Gln His Thr Lys Arg Ala Asp Trp
                340                 345                 350

Ser Val Lys Asn Pro Ser Ala Ala Pro Gly Gly Trp Gly Phe Ser Asn
                355                 360                 365

Ile Asn Thr Asn Asn Pro Asp Cys Asp Thr Ala Ala Val Leu Lys
370                 375                 380

Ala Ile Pro His Ser Tyr Ser Pro Ser Ala Trp Glu Arg Gly Val Ser
385                 390                 395                 400

Trp Leu Leu Ser Met Gln Asn Asp Gly Gly Phe Ser Ala Phe Glu
                405                 410                 415

Lys Asn Val Asn His Pro Leu Ile Arg Leu Leu Pro Leu Glu Ser Ala
                420                 425                 430

Glu Asp Ala Ala Val Asp Pro Ser Thr Ala Asp Leu Thr Gly Arg Val
                435                 440                 445

Leu His Phe Leu Gly Glu Lys Ala Gly Phe Thr Glu Lys His Gln His
450                 455                 460

Ile Gln Arg Ala Val Asn Trp Leu Phe Glu His Glu Gln Asn Gly
465                 470                 475                 480

Ser Trp Tyr Gly Arg Trp Gly Val Cys Tyr Ile Tyr Gly Thr Trp Ala
                485                 490                 495

Ala Leu Thr Gly Met His Ala Cys Glu Val Asp Arg Lys His Pro Ala
                500                 505                 510

Ile Gln Lys Ala Leu Arg Trp Leu Lys Ser Ile Gln His Asp Asp Gly
                515                 520                 525

Ser Trp Gly Glu Ser Cys Asn Ser Ala Glu Val Lys Thr Tyr Val Pro
530                 535                 540

Leu His Lys Gly Thr Ile Val Gln Thr Ala Trp Ala Leu Asp Ala Leu
545                 550                 555                 560

Leu Thr Tyr Glu Ser Ser Glu His Pro Ser Val Val Lys Gly Met Gln
                565                 570                 575

Tyr Leu Thr Asp Ser Ser Tyr His Gly Ala Asp Ser Leu Ala Tyr Pro
                580                 585                 590

Ala Gly Ile Gly Leu Pro Lys Gln Phe Tyr Ile Arg Tyr His Ser Tyr
                595                 600                 605

Pro Tyr Val Phe Ser Leu Leu Ala Val Gly Lys Tyr Leu Asn Ser Ile
610                 615                 620
```

Glu Lys Glu Thr Ala Asn Glu Thr
625                 630

<210> SEQ ID NO 3
<211> LENGTH: 592
<212> TYPE: PRT
<213> ORGANISM: Bacillus licheniformis

<400> SEQUENCE: 3

Met Thr Asp Ser Phe Phe Ile Leu Met Leu Thr Ser Leu Gly Asp Gln
1               5                   10                  15

Asp Ser Ser Leu Ile Ala Ser Leu Ala Glu Arg Ile Arg Ser Arg Gln
            20                  25                  30

Ser Glu Asp Gly Ala Phe Arg Asn His Pro Asp Glu Arg Ala Gly Asn
        35                  40                  45

Leu Thr Ala Thr Val Gln Gly Tyr Thr Gly Met Leu Ala Ser Gly Leu
    50                  55                  60

Tyr Asp Arg Lys Ala Pro His Met Gln Lys Ala Glu Ala Phe Ile Lys
65                  70                  75                  80

Asp Ala Gly Gly Leu Lys Gly Val His Phe Met Thr Lys Trp Met Leu
                85                  90                  95

Ala Ala Asn Gly Leu Tyr Pro Trp Pro Arg Ala Tyr Ile Pro Leu Ser
            100                 105                 110

Phe Leu Leu Ile Pro Ser Tyr Phe Pro Leu His Phe Tyr His Phe Ser
        115                 120                 125

Thr Tyr Ala Arg Ile His Phe Val Pro Met Ala Ile Thr Phe Asn Arg
    130                 135                 140

Arg Phe Ser Leu Lys Asn Asn Gln Ile Gly Ser Leu Arg His Leu Asp
145                 150                 155                 160

Glu Ala Met Ser Lys Asn Pro Leu Glu Trp Leu Asn Ile Arg Ala Phe
                165                 170                 175

Asp Glu Arg Thr Phe Tyr Ser Phe Asn Leu Gln Trp Lys Gln Leu Phe
            180                 185                 190

Gln Trp Pro Ala Tyr Val His Gln Leu Gly Phe Glu Ala Gly Lys Lys
        195                 200                 205

Tyr Met Leu Asp Arg Ile Glu Glu Asp Gly Thr Leu Tyr Ser Tyr Ala
    210                 215                 220

Ser Ala Thr Met Phe Met Ile Tyr Ser Leu Leu Ala Met Gly Ile Ser
225                 230                 235                 240

Lys Asn Ala Pro Val Val Lys Lys Ala Val Ser Gly Ile Lys Ser Leu
                245                 250                 255

Ile Ser Ser Cys Gly Lys Glu Gly Ala His Leu Glu Asn Ser Thr Ser
            260                 265                 270

Thr Val Trp Asp Thr Ala Leu Ile Ser Tyr Ala Met Gln Glu Ser Gly
        275                 280                 285

Val Pro Glu Gln His Ser Ser Thr Ser Ser Ala Ala Asp Tyr Leu Leu
    290                 295                 300

Lys Arg Gln His Val Lys Lys Ala Asp Trp Ala Val Ser Asn Pro Gln
305                 310                 315                 320

Ala Val Pro Gly Gly Trp Gly Phe Ser His Ile Asn Thr Asn Asn Pro
                325                 330                 335

Asp Leu Asp Asp Thr Ala Ala Leu Lys Ala Ile Pro Phe Gln Arg
            340                 345                 350

Arg Pro Asp Ala Trp Asn Arg Gly Leu Ala Trp Leu Leu Ser Met Gln

```
            355                 360                 365
Asn Lys Asp Gly Gly Phe Ala Ala Phe Glu Lys Asp Val Asp His Pro
        370                 375                 380

Leu Ile Arg Asn Leu Pro Leu Glu Ser Ala Ala Glu Ala Ala Val Asp
385                 390                 395                 400

Pro Ser Thr Ala Asp Leu Thr Gly Arg Val Leu His Leu Leu Gly Leu
                405                 410                 415

Lys Gly Arg Phe Thr Asp Asn His Pro Ala Val Arg Arg Ala Leu Arg
            420                 425                 430

Trp Leu Asp His His Gln Lys Ala Asp Gly Ser Trp Tyr Gly Arg Trp
        435                 440                 445

Gly Val Cys Phe Ile Tyr Gly Thr Trp Ala Ala Leu Thr Gly Met Lys
    450                 455                 460

Ala Val Gly Val Ser Ala Asn Gln Thr Ser Val Lys Lys Ala Ile Ser
465                 470                 475                 480

Trp Leu Lys Ser Ile Gln Arg Glu Asp Gly Ser Trp Gly Glu Ser Cys
                485                 490                 495

Lys Ser Cys Glu Ala Lys Arg Phe Val Pro Leu His Phe Gly Thr Val
            500                 505                 510

Val Gln Ser Ser Trp Ala Leu Glu Ala Leu Leu Gln Tyr Glu Arg Pro
        515                 520                 525

Asp Asp Pro Gln Ile Ile Lys Gly Ile Arg Phe Leu Ile Asp Glu His
530                 535                 540

Glu Ser Ser Arg Glu Arg Leu Glu Tyr Pro Thr Gly Ile Gly Leu Pro
545                 550                 555                 560

Asn Gln Phe Tyr Ile Arg Tyr His Ser Tyr Pro Phe Val Phe Ser Leu
                565                 570                 575

Leu Ala Ser Ser Ala Phe Ile Lys Lys Ala Glu Met Arg Glu Thr Tyr
            580                 585                 590

<210> SEQ ID NO 4
<211> LENGTH: 631
<212> TYPE: PRT
<213> ORGANISM: Alicyclobacillus acidocaldarius

<400> SEQUENCE: 4

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140
```

-continued

```
Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
            165                 170                 175

Leu Ser Ile Val Met Ser Arg Gln Pro Val Phe Pro Leu Pro Glu Arg
                180                 185                 190

Ala Arg Val Pro Glu Leu Tyr Glu Thr Asp Val Pro Arg Arg Arg
        195                 200                 205

Gly Ala Lys Gly Gly Gly Trp Ile Phe Asp Ala Leu Asp Arg Ala
        210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
                260                 265                 270

Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
        290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Trp Ala
        370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Ser Glu Asp Val
        435                 440                 445

Thr Ala His Val Leu Glu Cys Phe Gly Ser Phe Gly Tyr Asp Asp Ala
        450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
            485                 490                 495

Thr Gly Ala Val Val Ser Ala Leu Lys Ala Val Gly Ile Asp Thr Arg
                500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
        530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
```

```
                    565                 570                 575
Gly Val Gln Tyr Leu Val Glu Thr Gln Arg Pro Asp Gly Trp Asp
                580                 585                 590

Glu Pro Tyr Tyr Thr Gly Thr Gly Phe Pro Gly Asp Phe Tyr Leu Gly
            595                 600                 605

Tyr Thr Met Tyr Arg His Val Phe Pro Thr Leu Ala Leu Gly Arg Tyr
            610                 615                 620

Lys Gln Ala Ile Glu Arg Arg
625                 630

<210> SEQ ID NO 5
<211> LENGTH: 625
<212> TYPE: PRT
<213> ORGANISM: Bacillus megaterium

<400> SEQUENCE: 5

Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110

Arg Tyr Ile Ile Asp Ser Gly Gly Ile Ser Arg Ala His Phe Leu Thr
        115                 120                 125

Arg Trp Met Leu Ser Val Asn Gly Leu Tyr Glu Trp Pro Lys Leu Phe
    130                 135                 140

Tyr Leu Pro Leu Ser Leu Leu Val Pro Thr Tyr Val Pro Leu Asn
145                 150                 155                 160

Phe Tyr Glu Leu Ser Thr Ala Ala Arg Ile His Phe Val Pro Met Met
                165                 170                 175

Val Ala Gly Asn Lys Lys Phe Ser Leu Thr Ser Arg His Thr Pro Ser
            180                 185                 190

Leu Ser His Leu Asp Val Arg Glu Gln Lys Gln Ser Glu Glu Thr
        195                 200                 205

Thr Gln Glu Ser Arg Ala Ser Ile Phe Leu Val Asp His Leu Lys Gln
    210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
        275                 280                 285

Ser Leu Leu Ser Thr Cys Ser Gly His Val His Val Glu Asn Ser Thr
    290                 295                 300
```

```
Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
        355                 360                 365

Pro Asp Leu Asp Cys Thr Ser Ala Ala Ile Arg Ala Leu Ser Arg Arg
370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
                420                 425                 430

Lys Asp Ala Ala Thr Asp Pro Ala Thr Ala Asp Leu Thr Gly Arg Val
            435                 440                 445

Leu Glu Cys Leu Gly Asn Phe Ala Gly Met Asn Lys Ser His Pro Ser
450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
                500                 505                 510

Ile Ile Lys Ala Ile Asn Trp Leu Lys Ser Ile Gln Gln Glu Asp Gly
            515                 520                 525

Gly Phe Gly Glu Ser Cys Tyr Ser Ala Ser Leu Lys Lys Tyr Val Pro
            530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
                565                 570                 575

Phe Leu Leu Asn Pro Asn Leu Thr Glu Gln Gln Thr His Tyr Pro Thr
                580                 585                 590

Gly Ile Gly Leu Pro Gly Gln Phe Tyr Ile Gln Tyr His Ser Tyr Asn
            595                 600                 605

Asp Ile Phe Pro Leu Leu Ala Leu Ala His Tyr Ala Lys Lys His Ser
610                 615                 620

Ser
625

<210> SEQ ID NO 6
<211> LENGTH: 625
<212> TYPE: PRT
<213> ORGANISM: Bacillus megaterium

<400> SEQUENCE: 6

Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45
```

```
Thr Phe Asp Leu Asp Lys Glu Val Leu Ile Lys Gln Leu Thr Glu Arg
    50              55                  60
Ile Val Ser Leu Gln Asn Glu Asp Gly Leu Trp Thr Leu Phe Asp Asp
65                  70                  75                  80
Glu Glu His Asn Leu Ser Ala Thr Ile Gln Ala Tyr Thr Ala Leu Leu
                85                  90                  95
Tyr Ser Gly Tyr Tyr Gln Lys Asn Asp Arg Ile Leu Arg Lys Ala Glu
            100                 105                 110
Arg Tyr Ile Ile Asp Ser Gly Gly Ile Ser Arg Ala His Phe Leu Thr
        115                 120                 125
Arg Trp Met Leu Ser Val Asn Gly Leu Tyr Glu Trp Pro Lys Leu Phe
    130                 135                 140
Tyr Leu Pro Leu Ser Leu Leu Val Pro Thr Tyr Val Pro Leu Asn
145                 150                 155                 160
Phe Tyr Glu Leu Ser Thr Tyr Ala Arg Ile His Phe Val Pro Met Met
                165                 170                 175
Val Ala Gly Asn Lys Lys Phe Ser Leu Thr Ser Arg His Thr Pro Ser
            180                 185                 190
Leu Ser His Leu Asp Val Arg Glu Gln Lys Gln Glu Ser Glu Thr
        195                 200                 205
Thr Gln Glu Ser Arg Ala Ser Ile Phe Leu Val Asp His Leu Lys Gln
    210                 215                 220
Leu Ala Ser Leu Pro Ser Tyr Ile His Lys Leu Gly Tyr Gln Ala Ala
225                 230                 235                 240
Glu Arg Tyr Met Leu Glu Arg Ile Glu Lys Asp Gly Thr Leu Tyr Ser
                245                 250                 255
Tyr Ala Thr Ser Thr Phe Phe Met Ile Tyr Gly Leu Leu Ala Leu Gly
            260                 265                 270
Tyr Lys Lys Asp Ser Phe Val Ile Gln Lys Ala Ile Asp Gly Ile Cys
        275                 280                 285
Ser Leu Leu Ser Thr Cys Ser Gly His Val His Val Glu Asn Ser Thr
    290                 295                 300
Ser Thr Val Trp Asp Thr Ala Leu Leu Ser Tyr Ala Leu Gln Glu Ala
305                 310                 315                 320
Gly Val Pro Gln Gln Asp Pro Met Ile Lys Gly Thr Thr Arg Tyr Leu
                325                 330                 335
Lys Lys Arg Gln His Thr Lys Leu Gly Asp Trp Gln Phe His Asn Pro
            340                 345                 350
Asn Thr Ala Pro Gly Gly Trp Gly Phe Ser Asp Ile Asn Thr Asn Asn
        355                 360                 365
Pro Asp Leu Asp Cys Thr Ser Ala Ala Ile Arg Ala Leu Ser Arg Arg
    370                 375                 380
Ala Gln Thr Asp Thr Asp Tyr Leu Glu Ser Trp Gln Arg Gly Ile Asn
385                 390                 395                 400
Trp Leu Leu Ser Met Gln Asn Lys Asp Gly Gly Phe Ala Ala Phe Glu
                405                 410                 415
Lys Asn Thr Asp Ser Ile Leu Phe Thr Tyr Leu Pro Leu Glu Asn Ala
            420                 425                 430
Lys Asp Ala Ala Thr Asp Pro Ala Thr Ala Asp Leu Thr Gly Arg Val
        435                 440                 445
Leu Glu Cys Leu Gly Asn Phe Ala Gly Met Asn Lys Ser His Pro Ser
450                 455                 460
```

```
Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
            485                 490                 495

Ala Ile Thr Gly Leu Arg Ala Val Gly Val Ser Ala Ser Asp Pro Arg
        500                 505                 510

Ile Ile Lys Ala Ile Asn Trp Leu Lys Ser Ile Gln Gln Glu Asp Gly
    515                 520                 525

Gly Phe Gly Glu Ser Cys Tyr Ser Ala Ser Leu Lys Lys Tyr Val Pro
530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
                565                 570                 575

Phe Leu Leu Asn Pro Asn Leu Thr Glu Gln Gln Thr His Tyr Pro Thr
                580                 585                 590

Gly Ile Gly Ala Pro Gly Gln Phe Tyr Ile Gln Tyr His Ser Tyr Asn
            595                 600                 605

Asp Ile Phe Pro Leu Leu Ala Leu Ala His Tyr Ala Lys Lys His Ser
    610                 615                 620

Ser
625

<210> SEQ ID NO 7
<211> LENGTH: 1878
<212> TYPE: DNA
<213> ORGANISM: Bacillus megaterium

<400> SEQUENCE: 7
gtgattattc tgctgaaaga ggttcagctg gagatccagc gtcgcatcgc ctatttacgc      60
ccgacccaga aaaatgacgg cagtttccgc tactgcttcg agaccggcgt gatgccggac     120
gcctttctga ttatgctgct gcgtaccttc gacctggaca agaagttcct gattaagcag     180
ttaaccgagc gcattgtgag cctgcagaac gaagatggtc tgtggacact gtttgacgat     240
gaggagcaca acctgagtgc cacaatccag gcctataccg ccctgctgta cagcggctat     300
taccagaaaa atgaccgcat cttacgtaag gccgaacgct acattatcga tagcggcggc     360
atcagccgtg cacatttcct gacccgttgg atgctgagcg ttaatggcct gtacgaatgg     420
ccgaagctgt tctacctgcc gttaagcctg ctgctggttc gacctacgt gccgctgaac      480 ttttatgagc tgagcaccgc agcccgtatt cactttgttc cgatgatggt ggccggtaat     540
aaaaaattca gcttaaccag ccgccatacc ctagtctga gccacctgga tgtgcgtgaa      600
caaaaacagg agagtgaaga aaccacccag gagagccgcg caagcatctt cttagtggat     660
catctgaaac agctggccag cctgccgagt tacattcata agctgggcta ccaggcagca     720
gaacgctata tgctggaacg catcgaaaag gacggcacac tgtacagtta cgccaccagc     780
acctttttta tgatttacgg cctgctggcc ctgggctaca aaaaggatag ctttgtgatt     840
cagaaagcaa ttgatggcat ttgtagtctg ctgagtacat gcagcggtca cgtgcacgtt     900
gaaaacagta ccagcaccgt ttgggacacc gcactgctga ctatgccct gcaagaagca      960 ggcgtgccgc agcaggaccc gatgattaag ggtaccaccc gttatctgaa gaaacgccag    1020
catacaaaac tgggcgactg gcagtttcac aatccgaaca ccgcaccggg cggttggggc    1080
tttagcgaca ttaacaccaa caatcctgat ctggattgca ccagcgccgc aattcgtgca    1140
```

-continued

| | |
|---|---|
| ttaagccgcc gcgcccagac cgacacagat tacctggaaa gctggcagcg cggcatcaat | 1200 |
| tggctgctga gcatgcagaa caaggacggc ggctttgccg catttgaaaa gaacaccgat | 1260 |
| agtatcctgt tcacctacct gcctctggaa aatgcaaagg atgccgcaac cgatccggcc | 1320 |
| accgccgatt taaccggccg cgttttagaa tgcctgggta acttcgccgg catgaacaaa | 1380 |
| agccatccga gcattaaagc cgccgtgaaa tggctgttcg accaccagct ggataacggt | 1440 |
| agctggtacg tcgttgggg cgtgtgctat atttacggca cctgggccgc aatcacaggt | 1500 |
| ctgcgcgccg tgggtgttag tgccagcgat ccgcgtatca tcaaggcaat caactggctg | 1560 |
| aaaagcattc agcaagaaga tggtggcttt ggcgaaagct gctacagcgc cagcctgaaa | 1620 |
| aagtatgttc cgctgagttt cagcaccccg agtcagacag cctgggcact ggacgccctg | 1680 |
| atgaccattt gcccgttaaa ggatcagagc gttgaaaagg gcattaaatt cctgctgaat | 1740 |
| ccgaacctga cagagcaaca gacacactat ccgacaggca ttggtctgcc gggccagttc | 1800 |
| tatattcagt accacagcta caatgatatc tttcctttac tggccctggc ccactacgca | 1860 |
| aaaaagcata gtagctaa | 1878 |

<210> SEQ ID NO 8
<211> LENGTH: 1878
<212> TYPE: DNA
<213> ORGANISM: Bacillus megaterium

<400> SEQUENCE: 8

| | |
|---|---|
| gtgattattc tgctgaaaga ggttcagctg gagatccagc gtcgcatcgc ctatttacgc | 60 |
| ccgacccaga aaaatgacgg cagtttccgc tactgcttcg agaccggcgt gatgccggac | 120 |
| gcctttctga ttatgctgct gcgtaccttc gacctggaca agaagttct gattaagcag | 180 |
| ttaaccgagc gcattgtgag cctgcagaac gaagatggtc tgtggacact gtttgacgat | 240 |
| gaggagcaca acctgagtgc cacaatccag gcctataccg ccctgctgta cagcggctat | 300 |
| taccagaaaa atgaccgcat cttacgtaag gccgaacgct acattatcga tagcggcggc | 360 |
| atcagccgtg cacatttcct gacccgttgg atgctgagcg ttaatggcct gtacgaatgg | 420 |
| ccgaagctgt tctacctgcc gttaagcctg ctgctggttc cgacctacgt gccgctgaac | 480 |
| ttttatgagc tgagcaccta tgcccgtatt cactttgttc cgatgatggt ggccggtaat | 540 |
| aaaaaattca gcttaaccag ccgccatacc cctagtctga gccacctgga tgtgcgtgaa | 600 |
| caaaaacagg agagtgaaga aaccacccag gagagccgcg caagcatctt cttagtggat | 660 |
| catctgaaac agctggccag cctgccgagt tacattcata agctgggcta ccaggcagca | 720 |
| gaacgctata tgctggaacg catcgaaaag gacggcacac tgtacagtta cgccaccagc | 780 |
| accttttta tgatttacgg cctgctggcc ctgggctaca aaaaggatag ctttgtgatt | 840 |
| cagaaagcaa ttgatggcat tgtagtctg ctgagtacat gcagcggtca cgtgcacgtt | 900 |
| gaaaacagta ccagcaccgt ttgggacacc gcactgctga gctatgccct gcaagaagca | 960 |
| ggcgtgccgc agcaggaccc cgatgattaag ggtaccaccc gttatctgaa gaaacgccag | 1020 |
| catacaaaac tgggcgactg gcagtttcac aatccgaaca ccgcaccggg cggttggggc | 1080 |
| tttagcgaca ttaacaccaa caatcctgat ctggattgta ccagcgccgc aattcgtgca | 1140 |
| ttaagccgcc gcgcccagac cgacacagat tacctggaaa gctggcagcg cggcatcaat | 1200 |
| tggctgctga gcatgcagaa caaggacggc ggctttgccg catttgaaaa gaacaccgat | 1260 |
| agtatcctgt tcacctacct gcctctggaa aatgcaaagg atgccgcaac cgatccggcc | 1320 |
| accgccgatt taaccggccg cgttttagaa tgcctgggta acttcgccgg catgaacaaa | 1380 |

```
agccatccga gcattaaagc cgccgtgaaa tggctgttcg accaccagct ggataacggt    1440
agctggtacg gtcgttgggg cgtgtgctat atttacggca cctgggccgc aatcacaggt    1500
ctgcgcgccg tgggtgttag tgccagcgat ccgcgtatca tcaaggcaat caactggctg    1560
aaaagcattc agcaagaaga tggtggcttt ggcgaaagct gctacagcgc cagcctgaaa    1620
aagtatgttc cgctgagttt cagcaccccg agtcagacag cctgggcact ggacgccctg    1680
atgaccattt gcccgttaaa ggatcagagc gttgaaaagg gcattaaatt cctgctgaat    1740
ccgaacctga cagagcaaca gacacactat ccgacaggca ttggtgcacc gggccagttc    1800
tatattcagt accacagcta caatgatatc tttcctttac tggccctggc ccactacgca    1860
aaaaagcata gtagctaa                                                 1878
```

<210> SEQ ID NO 9
<211> LENGTH: 625
<212> TYPE: PRT
<213> ORGANISM: Bacillus megaterium

<400> SEQUENCE: 9

```
Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110

Arg Tyr Ile Ile Asp Ser Gly Gly Ile Ser Arg Ala His Phe Leu Thr
        115                 120                 125

Arg Trp Met Leu Ser Val Asn Gly Leu Tyr Glu Trp Pro Lys Leu Phe
    130                 135                 140

Tyr Leu Pro Leu Ser Leu Leu Val Pro Thr Tyr Val Pro Leu Asn
145                 150                 155                 160

Phe Tyr Glu Leu Ser Thr Tyr Ala Arg Ile His Phe Val Pro Met Met
                165                 170                 175

Val Ala Gly Asn Lys Lys Phe Ser Leu Thr Ser Arg His Thr Pro Ser
            180                 185                 190

Leu Ser His Leu Asp Val Arg Glu Gln Lys Gln Glu Ser Glu Glu Thr
        195                 200                 205

Thr Gln Glu Ser Arg Ala Ser Ile Phe Leu Val Asp His Leu Lys Gln
    210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
```

```
                    275                 280                 285
Ser Leu Leu Ser Thr Cys Ser Gly His Val His Val Glu Asn Ser Thr
    290                 295                 300

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
        355                 360                 365

Pro Asp Leu Asp Asp Thr Ser Ala Ala Ile Arg Ala Leu Ser Arg Arg
    370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
            420                 425                 430

Lys Asp Ala Ala Thr Asp Pro Ala Thr Ala Asp Leu Thr Gly Arg Val
        435                 440                 445

Leu Glu Cys Leu Gly Asn Phe Ala Gly Met Asn Lys Ser His Pro Ser
    450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
            500                 505                 510

Ile Ile Lys Ala Ile Asn Trp Leu Lys Ser Ile Gln Gln Glu Asp Gly
        515                 520                 525

Gly Phe Gly Glu Ser Cys Tyr Ser Ala Ser Leu Lys Lys Tyr Val Pro
    530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
                565                 570                 575

Phe Leu Leu Asn Pro Asn Leu Thr Glu Gln Gln Thr His Tyr Pro Thr
            580                 585                 590

Gly Ile Gly Ala Pro Gly Gln Phe Tyr Ile Gln Tyr His Ser Tyr Asn
        595                 600                 605

Asp Ile Phe Pro Leu Leu Ala Leu Ala His Tyr Ala Lys Lys His Ser
    610                 615                 620

Ser
625

<210> SEQ ID NO 10
<211> LENGTH: 625
<212> TYPE: PRT
<213> ORGANISM: Bacillus megaterium

<400> SEQUENCE: 10

Met Ile Ile Leu Leu Lys Glu Val Gln Leu Glu Ile Gln Arg Arg Ile
1               5                   10                  15
```

-continued

```
Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110

Arg Tyr Ile Ile Asp Ser Gly Gly Ile Ser Arg Ala His Phe Leu Thr
        115                 120                 125

Arg Trp Met Leu Ser Val Asn Gly Leu Tyr Glu Trp Pro Lys Leu Phe
    130                 135                 140

Tyr Leu Pro Leu Ser Leu Leu Val Pro Thr Tyr Val Pro Leu Asn
145                 150                 155                 160

Phe Tyr Glu Leu Ser Thr Tyr Ala Arg Ile His Phe Val Pro Met Met
                165                 170                 175

Val Ala Gly Asn Lys Lys Phe Ser Leu Thr Ser Arg His Thr Pro Ser
            180                 185                 190

Leu Ser His Leu Asp Val Arg Glu Gln Lys Gln Ser Glu Glu Thr
        195                 200                 205

Thr Gln Glu Ser Arg Ala Ser Ile Phe Leu Val Asp His Leu Lys Gln
210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
        275                 280                 285

Ser Leu Leu Ser Thr Cys Ser Gly His Val His Val Glu Asn Ser Thr
    290                 295                 300

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
        355                 360                 365

Pro Asp Leu Asp Asp Thr Ser Ala Ala Ile Arg Ala Leu Ser Arg Arg
    370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
            420                 425                 430

Lys Asp Ala Ala Thr Asp Pro Ala Thr Ala Asp Leu Thr Gly Arg Val
```

```
                      435                 440                 445
Leu Glu Cys Leu Gly Asn Phe Ala Gly Met Asn Lys Ser His Pro Ser
450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
            500                 505                 510

Ile Ile Lys Ala Ile Asn Trp Leu Lys Ser Ile Gln Gln Glu Asp Gly
            515                 520                 525

Gly Phe Gly Glu Ser Cys Tyr Ser Ala Ser Leu Lys Lys Tyr Val Pro
            530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
                565                 570                 575

Phe Leu Leu Asn Pro Asn Leu Thr Glu Gln Gln Thr His Tyr Pro Thr
                580                 585                 590

Gly Ile Gly Phe Pro Gly Gln Phe Tyr Ile Gln Tyr His Ser Tyr Asn
            595                 600                 605

Asp Ile Phe Pro Leu Leu Ala Leu Ala His Tyr Ala Lys Lys His Ser
610                 615                 620

Ser
625

<210> SEQ ID NO 11
<211> LENGTH: 1878
<212> TYPE: DNA
<213> ORGANISM: Bacillus megaterium

<400> SEQUENCE: 11
gtgattattc tgctgaaaga ggttcagctg agatccagc gtcgcatcgc ctatttacgc         60
ccgacccaga aaaatgacgg cagtttccgc tactgcttcg agaccggcgt gatgccggac       120
gcctttctga ttatgctgct gcgtaccttc gacctggaca agaagttct gattaagcag        180 ttaaccgagc gcattgtgag cctgcagaac aagatggtc tgtggacact gtttgacgat       240
gaggagcaca acctgagtgc cacaatccag gcctataccg ccctgctgta cagcggctat      300
taccagaaaa atgaccgcat cttacgtaag gccgaacgct acattatcga tagcggcggc     360
atcagccgtg cacatttcct gacccgttgg atgctgagcg ttaatggcct gtacgaatgg     420
ccgaagctgt tctacctgcc gttaagcctg ctgctggttc cgacctacgt gccgctgaac     480
ttttatgagc tgagcaccta tgcccgtatt cactttgttc gatgatggt ggccggtaat      540 aaaaaattca gcttaaccag ccgccatacc cctagtctga gccacctgga tgtgcgtgaa    600
caaaaacagg agagtgaaga aaccaccag gagagccgcg caagcatctt cttagtggat      660
catctgaaac agctggccag cctgccgagt tacattcata agctgggcta ccaggcagca     720
gaacgctata tgctggaacg catcgaaaag gacggcacac tgtacagtta cgccaccagc      780
acctttttta tgatttacgg cctgctggcc ctgggctaca aaaaggatag ctttgtgatt      840
cagaaagcaa ttgatggcat ttgtagtctg ctgagtacat gcagcggtca cgtgcacgtt     900
gaaaacagta ccagcaccgt ttgggacacc gcactgctga gctatgccct gcaagaagca     960
ggcgtgccgc agcaggaccc cgatgattaag ggtaccaccc gttatctgaa gaaacgccag   1020
```

```
catacaaaac tgggcgactg gcagtttcac aatccgaaca ccgcaccggg cggttggggc    1080
tttagcgaca ttaacaccaa caatcctgat ctggatgata ccagcgccgc aattcgtgca    1140
ttaagccgcc gcgcccagac cgacacagat tacctggaaa gctggcagcg cggcatcaat    1200
tggctgctga gcatgcagaa caaggacggc ggctttgccg catttgaaaa gaacaccgat    1260
agtatcctgt tcacctacct gcctctggaa aatgcaaagg atgccgcaac cgatccggcc    1320
accgccgatt taaccggccg cgttttagaa tgcctgggta acttcgccgg catgaacaaa    1380
agccatccga gcattaaagc cgccgtgaaa tggctgttcg accaccagct ggataacggt    1440
agctggtacg gtcgttgggg cgtgtgctat atttacggca cctgggccgc aatcacaggt    1500
ctgcgcgccg tgggtgttag tgccagcgat ccgcgtatca tcaaggcaat caactggctg    1560
aaaagcattc agcaagaaga tggtggcttt ggcgaaagct gctacagcgc cagcctgaaa    1620
aagtatgttc cgctgagttt cagcaccccg agtcagacag cctgggcact ggacgccctg    1680
atgaccattt gcccgttaaa ggatcagagc gttgaaaagg gcattaaatt cctgctgaat    1740
ccgaacctga cagagcaaca gacacactat ccgacaggca ttggtgcacc gggccagttc    1800
tatattcagt accacagcta caatgatatc tttcctttac tggccctggc ccactacgca    1860
aaaaagcata gtagctaa                                                  1878

<210> SEQ ID NO 12
<211> LENGTH: 1878
<212> TYPE: DNA
<213> ORGANISM: Bacillus megaterium

<400> SEQUENCE: 12
gtgattattc tgctgaaaga ggttcagctg gagatccagc gtcgcatcgc ctatttacgc      60
ccgacccaga aaatgacgg cagtttccgc tactgcttcg agaccggcgt gatgccggac     120
gcctttctga ttatgctgct gcgtaccttc gacctggaca agaagttct gattaagcag     180 ttaaccgagc gcattgtgag cctgcagaac gaagatggtc tgtggacact gtttgacgat     240
gaggagcaca acctgagtgc cacaatccag gcctataccg ccctgctgta cagcggctat     300
taccagaaaa atgaccgcat cttacgtaag gccgaacgct acattatcga tagcggcggc     360
atcagccgtg cacatttcct gacccgttgg atgctgagcg ttaatggcct gtacgaatgg     420
ccgaagctgt tctacctgcc gttaagcctg ctgctggttc cgacctacgt gccgctgaac     480
ttttatgagc tgagcaccta tgcccgtatt cactttgttc gatgatggt ggccggtaat     540 aaaaaattca gcttaaccag ccgccatacc cctagtctga gccacctgga tgtgcgtgaa     600
caaaaacagg agagtgaaga aaccacccag gagagccgcg caagcatctt cttagtggat     660
catctgaaac agctggccag cctgccgagt tacattcata gctgggcta ccaggcagca     720 gaacgctata tgctggaacg catcgaaaag gacggcacac tgtacagtta cgccaccagc     780 accttttta tgatttacgg cctgctggcc ctgggctaca aaaaggatag ctttgtgatt     840
cagaaagcaa ttgatggcat ttgtagtctg ctgagtacat gcagcggtca cgtgcacgtt     900
gaaaacagta ccagcaccgt ttgggacacc gcactgctga gctatgccct gcaagaagca     960
ggcgtgccgc agcaggaccc gatgattaag ggtaccaccc gttatctgaa gaaacgccag    1020
catacaaaac tgggcgactg gcagtttcac aatccgaaca ccgcaccggg cggttggggc    1080
tttagcgaca ttaacaccaa caatcctgat ctggatgata ccagcgccgc aattcgtgca    1140
ttaagccgcc gcgcccagac cgacacagat tacctggaaa gctggcagcg cggcatcaat    1200
```

```
tggctgctga gcatgcagaa caaggacggc ggctttgccg catttgaaaa gaacaccgat    1260
agtatcctgt tcacctacct gcctctggaa aatgcaaagg atgccgcaac cgatccggcc    1320
accgccgatt taaccggccg cgttttagaa tgcctgggta acttcgccgg catgaacaaa    1380
agccatccga gcattaaagc cgccgtgaaa tggctgttcg accaccagct ggataacggt    1440
agctggtacg tcgttgggg cgtgtgctat atttacggca cctgggccgc aatcacaggt    1500
ctgcgcgccg tgggtgttag tgccagcgat ccgcgtatca tcaaggcaat caactggctg    1560
aaaagcattc agcaagaaga tggtggcttt ggcgaaagct gctacagcgc cagcctgaaa    1620
aagtatgttc cgctgagttt cagcaccccg agtcagacag cctgggcact ggacgccctg    1680
atgaccattt gcccgttaaa ggatcagagc gttgaaaagg gcattaaatt cctgctgaat    1740
ccgaacctga cagagcaaca gacacactat ccgacaggca ttggttttcc gggccagttc    1800
tatattcagt accacagcta caatgatatc tttcctttac tggccctggc ccactacgca    1860
aaaaagcata gtagctaa                                                  1878
```

<210> SEQ ID NO 13
<211> LENGTH: 625
<212> TYPE: PRT
<213> ORGANISM: Bacillus megaterium

<400> SEQUENCE: 13

```
Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110

Arg Tyr Ile Ile Asp Ser Gly Gly Ile Ser Arg Ala His Phe Leu Thr
        115                 120                 125

Arg Trp Met Leu Ser Val Asn Gly Leu Tyr Glu Trp Pro Lys Leu Phe
    130                 135                 140

Tyr Leu Pro Leu Ser Leu Leu Val Pro Thr Tyr Val Pro Leu Asn
145                 150                 155                 160

Phe Tyr Glu Leu Ser Thr Tyr Ala Arg Ile His Phe Val Pro Met Met
                165                 170                 175

Val Ala Gly Asn Lys Lys Phe Ser Leu Thr Ser Arg His Thr Pro Ser
            180                 185                 190

Leu Ser His Leu Asp Val Arg Glu Gln Lys Gln Glu Ser Glu Glu Thr
        195                 200                 205

Thr Gln Glu Ser Arg Ala Ser Ile Phe Leu Val Asp His Leu Lys Gln
    210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255
```

```
Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
        275                 280                 285

Ser Leu Leu Ser Thr Cys Ser Gly His Val His Val Glu Asn Ser Thr
290                 295                 300

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
        355                 360                 365

Pro Asp Leu Asp Asp Thr Ser Ala Ala Ile Arg Ala Leu Ser Arg Arg
370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
            420                 425                 430

Lys Asp Ala Ala Thr Asp Pro Ala Thr Ala Asp Leu Thr Gly Arg Val
        435                 440                 445

Leu Glu Cys Leu Gly Asn Phe Ala Gly Met Asn Lys Ser His Pro Ser
450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
            500                 505                 510

Ile Ile Lys Ala Ile Asn Trp Leu Lys Ser Ile Gln Asn Glu Asp Gly
        515                 520                 525

Gly Phe Gly Glu Ser Cys Tyr Ser Ala Ser Leu Lys Lys Tyr Val Pro
530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
                565                 570                 575

Phe Leu Leu Asn Pro Asn Leu Thr Glu Gln Gln Thr His Tyr Pro Thr
            580                 585                 590

Gly Ile Gly Val Pro Gly Gln Phe Tyr Ile Gln Tyr His Ser Tyr Asn
        595                 600                 605

Asp Ile Phe Pro Leu Leu Ala Leu Ala His Tyr Ala Lys Lys His Ser
610                 615                 620

Ser
625

<210> SEQ ID NO 14
<211> LENGTH: 1878
<212> TYPE: DNA
<213> ORGANISM: Bacillus megaterium
```

<400> SEQUENCE: 14

```
gtgattattc tgctgaaaga ggttcagctg gagatccagc gtcgcatcgc ctatttacgc    60
ccgacccaga aaaatgacgg cagtttccgc tactgcttcg agaccggcgt gatgccggac   120
gcctttctga ttatgctgct gcgtaccttc gacctggaca agaagttct gattaagcag    180
ttaaccgagc gcattgtgag cctgcagaac gaagatggtc tgtggacact gtttgacgat   240
gaggagcaca acctgagtgc cacaatccag gcctataccg ccctgctgta cagcggctat   300
taccagaaaa atgaccgcat cttacgtaag gccgaacgct acattatcga tagcggcggc   360
atcagccgtg cacatttcct gacccgttgg atgctgagcg ttaatggcct gtacgaatgg   420
ccgaagctgt tctacctgcc gttaagcctg ctgctggttc cgacctacgt gccgctgaac   480
ttttatgagc tgagcaccta tgcccgtatt cactttgttc cgatgatggt ggccggtaat   540
aaaaaattca gcttaaccag ccgccatacc cctagtctga gccacctgga tgtgcgtgaa   600
caaaaacagg agagtgaaga aaccacccag gagagccgcg caagcatctt cttagtggat   660
catctgaaac agctggccag cctgccgagt tacattcata agctgggcta ccaggcagca   720
gaacgctata tgctggaacg catcgaaaag gacggcacac tgtacagtta cgccaccagc   780
accttttta tgatttacgg cctgctggcc ctgggctaca aaaaggatag ctttgtgatt   840
cagaaagcaa ttgatggcat ttgtagtctg ctgagtacat gcagcggtca cgtgcacgtt   900
gaaaacagta ccagcaccgt ttgggacacc gcactgctga gctatgccct gcaagaagca   960
ggcgtgccgc agcaggaccc gatgattaag ggtaccaccc gttatctgaa gaaacgccag  1020
catacaaaac tgggcgactg gcagtttcac aatccgaaca ccgcaccggg cggttggggc  1080
tttagcgaca ttaacaccaa caatcctgat ctggatgata ccagcgccgc aattcgtgca  1140
ttaagccgcc gcgcccagac cgacacagat tacctggaaa gctggcagcg cggcatcaat  1200
tggctgctga gcatgcagaa caaggacggc ggctttgccg catttgaaaa gaacaccgat  1260
agtatcctgt tcacctacct gcctctggaa aatgcaaagg atgccgcaac cgatccggcc  1320
accgccgatt taaccggccg cgttttagaa tgcctgggta acttcgccgg catgaacaaa  1380
agccatccga gcattaaagc cgccgtgaaa tggctgttcg accaccagct ggataacggt  1440
agctggtacg gtcgttgggg cgtgtgctat atttacggca cctgggccgc aatcacaggt  1500
ctgcgcgccg tgggtgttag tgccagcgat ccgcgtatca tcaaggcaat caactggctg  1560
aaaagcattc agcaagaaga tggtggcttt ggcgaaagct gctacagcgc cagcctgaaa  1620
aagtatgttc cgctgagttt cagcaccccg agtcagacag cctgggcact ggacgccctg  1680
atgaccattt gcccgttaaa ggatcagagc gttgaaaagg gcattaaatt cctgctgaat  1740
ccgaacctga cagagcaaca gacacactat ccgacaggca ttggtgttcc gggccagttc  1800
tatattcagt accacagcta caatgatatc tttcctttac tggccctggc ccactacgca  1860
aaaaagcata gtagctaa                                               1878
```